(12) United States Patent
Freeman et al.

(10) Patent No.: US 12,144,327 B2
(45) Date of Patent: Nov. 19, 2024

(54) METHODS AND SYSTEMS FOR SORTING AND IMAGING INSECTS

(71) Applicant: Pioneer Hi-Bred International, Inc., Johnston, IA (US)

(72) Inventors: Michael Freeman, Burlingame, CA (US); Kathleen Marie Harding, Redwood City, CA (US); Jingtong Hou, San Pablo, CA (US); Bumshik Robert Pak, Union City, CA (US); Phillip A. Patten, Portola Valley, CA (US); Lindsey Della Wiemer, Newark, CA (US); Takashi Yamamoto, Dublin, CA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 18/349,428

(22) Filed: Jul. 10, 2023

(65) Prior Publication Data
US 2023/0345921 A1    Nov. 2, 2023

Related U.S. Application Data

(60) Division of application No. 17/087,900, filed on Nov. 3, 2020, now Pat. No. 11,730,152, which is a continuation of application No. 15/491,454, filed on Apr. 19, 2017, now abandoned.

(60) Provisional application No. 62/325,253, filed on Apr. 20, 2016.

(51) Int. Cl.
| | | |
|---|---|---|
| A01K 67/033 | (2006.01) | |
| A01K 29/00 | (2006.01) | |
| B07C 5/342 | (2006.01) | |
| B25J 11/00 | (2006.01) | |
| B25J 19/02 | (2006.01) | |
| G01N 1/30 | (2006.01) | |
| G01N 21/95 | (2006.01) | |
| G06V 20/69 | (2022.01) | |
| G06V 40/10 | (2022.01) | |

(52) U.S. Cl.
CPC ............ *A01K 67/033* (2013.01); *A01K 29/00* (2013.01); *B07C 5/3425* (2013.01); *B07C 5/3427* (2013.01); *B25J 11/00* (2013.01); *B25J 19/021* (2013.01); *G01N 1/30* (2013.01); *G01N 21/951* (2013.01); *G06V 20/693* (2022.01); *G06V 40/103* (2022.01)

(58) Field of Classification Search
CPC ..... B07C 5/3425; B07C 5/3427; B07C 5/361; B07C 2501/0063; G01N 1/30; G01N 21/951; G06K 9/00134; G06K 9/00369; B25J 11/00; B25J 19/021; A01K 67/033
See application file for complete search history.

(56) References Cited

U.S. PATENT DOCUMENTS

| | | | | |
|---|---|---|---|---|
| 6,150,158 A * | 11/2000 | Bhide | ................ | A01H 4/001 |
| | | | | 435/286.3 |
| 6,517,856 B1 | 2/2003 | Roe et al. | | |
| 6,657,713 B2 * | 12/2003 | Hansen | ............ | G01N 15/1456 |
| | | | | 356/237.1 |
| 7,116,407 B2 * | 10/2006 | Hansen et al. | ..... | G01N 33/5085 |
| | | | | 356/73 |

(Continued)

*Primary Examiner* — Joseph C Rodriguez
(74) *Attorney, Agent, or Firm* — Ballard Spahr LLP

(57) ABSTRACT

Systems and methods for sorting and imaging insects, including egg and larval life stages, useful for automated high throughput bioassays.

21 Claims, 19 Drawing Sheets

(56) References Cited

U.S. PATENT DOCUMENTS

| | | | |
|---|---|---|---|
| 9,629,339 B2* | 4/2017 | Newton et al. | A01K 5/00 |
| 9,689,782 B2* | 6/2017 | Cargill | B65G 47/80 |
| 10,264,769 B2* | 4/2019 | Leo | A23K 20/163 |
| 11,730,152 B1* | 8/2023 | Freeman | B07C 5/3425 |
| | | | 382/110 |
| 2001/0036668 A1* | 11/2001 | Furlong | G01N 33/5005 |
| | | | 436/63 |
| 2002/0019004 A1 | 2/2002 | Orfao | |
| 2002/0142288 A1* | 10/2002 | Kaultkiewicz | G01N 15/14 |
| | | | 435/4 |
| 2008/0295774 A1* | 12/2008 | Van Beek et al. | A01K 67/033 |
| | | | 119/6.6 |
| 2015/0031066 A1* | 1/2015 | Malinouski | B01L 3/0293 |
| | | | 435/283.1 |
| 2017/0081632 A1* | 3/2017 | Shih | C12N 1/20 |
| 2018/0077912 A1 | 3/2018 | Comparat et al. | |
| 2020/0281164 A1* | 9/2020 | Lepek | A01M 1/026 |

\* cited by examiner

FIG. 10A

| IP1 | | | | IP2 | | | | IP3 | | | |
|---|---|---|---|---|---|---|---|---|---|---|---|
| Dose | Sample Size | Mean Size | 95%CL | Dose | Sample Size | Mean Size | 95%CL | Dose | Sample Size | Mean Size | 95%CL |
| 0.27 | 9 | 27245 | 2856 | 0.70 | 9 | 19344 | 3577 | 0.63 | 10 | 5667 | 2917 |
| 0.53 | 9 | 28330 | 4515 | 1.41 | 8 | 17999 | 3606 | 1.26 | 9 | 3147 | 776 |
| 1.06 | 8 | 25862 | 10479 | 2.82 | 10 | 8980 | 2950 | 2.51 | 8 | 2362 | 295 |
| 2.12 | 12 | 30527 | 4414 | 5.64 | 10 | 5579 | 2777 | 5.02 | 11 | 4746 | 357 |
| 4.24 | 11 | 28962 | 10121 | 11.28 | 8 | 3198 | 914 | 10.04 | 10 | 2323 | 583 |
| 8.48 | 10 | 24849 | 7738 | 22.55 | 11 | 1948 | 515 | 20.08 | 11 | 4746 | 5196 |
| 16.96 | 10 | 25209 | 5436 | 45.10 | 10 | 2456 | 854 | 40.16 | 4 | 2080 | 78 |
| 33.92 | 12 | 27614 | 3897 | 90.20 | 9 | 1987 | 618 | 80.33 | 11 | 2601 | 1054 |

FIG. 10B

| IP1 | | | | IP2 | | | | IP3 | | | |
|---|---|---|---|---|---|---|---|---|---|---|---|
| Dose | Sample Size | Mean Size | 95%CL | Dose | Sample Size | Mean Size | 95%CL | Dose | Sample Size | Mean Size | 95%CL |
| 0.27 | 15 | 17189 | 1953 | 0.70 | 13 | 23784 | 4573 | 0.63 | 12 | 2996 | 1083 |
| 0.53 | 12 | 10752 | 2530 | 1.41 | 15 | 21286 | 4469 | 1.26 | 15 | 1527 | 268 |
| 1.06 | 10 | 5833 | 2409 | 2.82 | 17 | 16387 | 3297 | 2.51 | 11 | 1562 | 506 |
| 2.12 | 15 | 3493 | 1486 | 5.64 | 13 | 11591 | 3566 | 5.02 | 12 | 1280 | 222 |
| 4.24 | 10 | 2175 | 565 | 11.28 | 14 | 6471 | 2693 | 10.04 | 17 | 2216 | 719 |
| 8.48 | 14 | 1774 | 337 | 22.55 | 14 | 4027 | 1788 | 20.08 | 15 | 1463 | 227 |
| 16.96 | 11 | 2282 | 940 | 45.10 | 13 | 4286 | 1695 | 40.16 | 12 | 1251 | 97 |
| 33.92 | 11 | 1630 | 358 | 90.20 | 18 | 3674 | 1103 | 80.33 | 14 | 1411 | 286 |

FIG. 11A

| | IP1 | | | IP2 | | | IP3 | |
|---|---|---|---|---|---|---|---|---|
| Dose | Sample Size | Percent Mortality | Dose | Sample Size | Percent Mortality | Dose | Sample Size | Percent Mortality |
| 0.27 | 10 | 10% | 0.70 | 9 | 0% | 0.63 | 10 | 0% |
| 0.53 | 9 | 0% | 1.41 | 8 | 0% | 1.26 | 10 | 20% |
| 1.06 | 8 | 13% | 2.82 | 11 | 9% | 2.51 | 10 | 30% |
| 2.12 | 12 | 0% | 5.64 | 10 | 10% | 5.02 | 11 | 82% |
| 4.24 | 11 | 0% | 11.28 | 8 | 88% | 10.04 | 10 | 90% |
| 8.48 | 10 | 10% | 22.55 | 11 | 82% | 20.08 | 12 | 92% |
| 16.96 | 10 | 0% | 45.10 | 10 | 90% | 40.16 | 5 | 100% |
| 33.92 | 12 | 0% | 90.20 | 9 | 100% | 80.33 | 11 | 91% |

FIG. 11B

| | IP1 | | | IP2 | | | IP3 | |
|---|---|---|---|---|---|---|---|---|
| Dose | Sample Size | Percent Mortality | Dose | Sample Size | Percent Mortality | Dose | Sample Size | Percent Mortality |
| 0.27 | 15 | 0% | 0.70 | 13 | 0% | 0.63 | 13 | 38% |
| 0.53 | 12 | 0% | 1.41 | 15 | 7% | 1.26 | 19 | 68% |
| 1.06 | 10 | 0% | 2.82 | 17 | 24% | 2.51 | 14 | 79% |
| 2.12 | 15 | 7% | 5.64 | 13 | 8% | 5.02 | 14 | 100% |
| 4.24 | 12 | 8% | 11.28 | 15 | 0% | 10.04 | 18 | 100% |
| 8.48 | 16 | 69% | 22.55 | 14 | 7% | 20.08 | 15 | 100% |
| 16.96 | 11 | 82% | 45.10 | 14 | 14% | 40.16 | 14 | 100% |
| 33.92 | 11 | 73% | 90.20 | 18 | 28% | 80.33 | 14 | 100% |

FIG. 12

| Insecticidal Protein | N | EC50 (ppm) | Upper 95CL | Lower 95CL | LC50 (ppm) | Upper 95CL | Lower 95CL | Dose used in LT50 | LT50 (days) | Upper 95CL | Lower 95CL |
|---|---|---|---|---|---|---|---|---|---|---|---|
| IP4 | 15 | 1.78 | 2.89 | 1.02 | 11.33 | 16.66 | 7.7 | 98 | 3.5 | 6.0 | 3.0 |
| IP2 | 16 | 1.99 | 2.79 | 1.35 | 11.57 | 16.81 | 7.97 | 95 | 3.0 | 5.0 | 3.0 |
| IP5 | 15 | 1.87 | 3.25 | 0.98 | 19.63 | 27.43 | 14.05 | 102 | 3.0 | NA | 2.0 |
| IP6 | 16 | 2.26 | 3.72 | 1.26 | 19.48 | 29.59 | 12.82 | 98 | 3.0 | 6.0 | 3.0 |
| IP7 | 15 | 1.58 | 2.98 | 0.75 | 17.84 | 26.27 | 12.11 | 113 | 3.5 | 6.0 | 3.0 |
| IP8 | 16 | 1.52 | 2.59 | 0.82 | 11.19 | 15.39 | 8.14 | 112 | 3.0 | 4.0 | 3.0 |

METHODS AND SYSTEMS FOR SORTING AND IMAGING INSECTS

CROSS-REFERENCE TO RELATED APPLICATION

This application is a division of U.S. patent application Ser. No. 17/087,900, filed Nov. 3, 2020, which is a continuation of U.S. patent application Ser. No. 15/491,454, filed Apr. 19, 2017, which claims priority to and the benefit of the filing date of U.S. Provisional Patent Application No. 62/325,253, filed Apr. 20, 2016. The entire contents of each of these applications are incorporate by reference herein.

FIELD

The present embodiments of the invention generally relate to methods and systems for sorting and imaging insects, including egg and larval life stages, useful for automated high throughput bioassays.

BACKGROUND

There has been a long felt need for compositions and methods for controlling or eradicating insect pests of agricultural significance. There is also a long felt need for high throughput methods and systems of screening candidate compositions and methods and systems for controlling or eradicating insect pests of agricultural significance.

BRIEF SUMMARY

Methods are provided for sorting insects. In some embodiments, methods are provided for sorting insects having a high hatch rate comprising rinsing insects with a rinse solution; discarding floating insects from the rinse solution; sterilizing the insects; separating immature insects from mature insects; and sorting the mature insects using a sorting system. In another embodiment, a method is provided for sorting insects having a high hatch rate comprising removing insect clumps; incubating the insects until the insects show signs of development; and sorting the mature insects using sorting system.

In another embodiment, methods are provided for assaying insects. In some embodiments, methods are provided for assaying insects comprising placing an insect into a well of an assay plate; capturing an image of the well of the assay plate; and determining a metric measurement of the insect in the well of the assay plate. In one embodiment, the metric measurement of the insect comprises the use of the pixel count of the image.

Another embodiment relates to a method for preparing insects for a bioassay. In some embodiments, methods are provided for preparing insects for bioassay comprising preparing individually dispersed insects; and dispensing a pre-determined number of individually dispersed insects into each well of an assay plate.

Methods are provided for assaying the activity of insecticidal compounds using an automated system. In some embodiments, methods are provided relating to assaying the activity of insecticidal compounds using an automated system comprising providing a multi-well plate with at least one insect in a predetermined number of wells of a multi-well plate; transporting by automated means the multi-well plate to an incubation device for incubation of the multi-well plate; and transporting by automated means the multi-well plate to a measuring device for measuring movement or determining a metric measurement.

Methods are provided for sorting insect eggs. In some embodiments, methods are provided for sorting insect eggs having a high hatch rate comprising rinsing insect eggs with a rinse solution; discarding floating insect eggs from the rinse solution; sterilizing the insect eggs; separating immature insect eggs from mature insect eggs; and sorting the mature insect eggs using a sorting system. In another embodiment, a method is provided for sorting insect eggs having a high hatch rate comprising removing insect eggs clumps; incubating the insect eggs until the insect eggs show signs of development; and sorting the mature insect eggs using sorting system.

In another embodiment, methods are provided for assaying insects. In some embodiments, methods are provided for assaying insects comprising placing an insect egg into a well of an assay plate; capturing an image of the well of the assay plate; and determining a metric measurement of the insect in the well of the assay plate. In one embodiment, the metric measurement of the insect comprises the use of the pixel count of the image.

Another embodiment relates to a method for preparing insect eggs for a bioassay. In some embodiments, methods are provided for preparing insect eggs for bioassay comprising preparing individually dispersed insect eggs; selecting insect eggs which are ready to hatch within a predetermined time frame; and dispensing a pre-determined number of individually dispersed insect eggs into each well of an assay plate.

Methods are provided for assaying the activity of insecticidal compounds using an automated system. In some embodiments, methods are provided relating to assaying the activity of insecticidal compounds using an automated system comprising providing a multi-well plate with at least one insect eggs in a predetermined number of wells of a multi-well plate; transporting by automated means the multi-well plate to an incubation device for incubation of the multi-well plate; and transporting by automated means the multi-well plate to a measuring device for measuring movement or determining a metric measurement.

In another embodiment, an automation system for assaying the activity of insecticidal compounds in a high throughput mode is provided. In some embodiments, an automation system for assaying the activity of insecticidal compounds in a high throughput mode comprises a sorting system capable of dispensing insect eggs into a multi-well plate, wherein the insect eggs maintain a high hatch rate; an automated means for transporting the multi-well plate; a measuring device, wherein the measuring device is capable of measuring movement or determining a metric measurement; and a programmable control device, wherein the programmable control device is capable of coordinating the functions and timings of the automation system.

In another embodiment, the methods provided relate to an automated method for placing a preset number of insect eggs in each well of a multi-well plate. In some embodiments, an automated method for placing a preset number of insect eggs in each well of a multi-well plate comprises preparing insect eggs to increase hatch rate and reduced variability in hatching time; selecting insect eggs capable of hatching within a predetermined time frame using a sorting system; and dispensing a preset number of the selected insect eggs into a well of a multi-well plate using a sorter system.

DESCRIPTION OF FIGURES

FIG. 10A is a chart showing insecticidal protein bioassay IC-50 dose response results using three different insecticidal proteins (IP1-3) using the automated assay system, including larval size 4 days after infest for CEW. FIG. 10B is a chart showing insecticidal protein bioassay IC-50 dose response results using three different insecticidal proteins (IP1-3) using the automated assay system, including larval size 4 days after infest for FAW. Mean pixel area for each replicate dose and 95% confidence limit (CL) is shown.

FIG. 11A is a chart showing insecticidal protein bioassay LC-50 dose response results using three different insecticidal proteins (IP1-3) using the automated assay system, including larval mortality 6 days after infest for CEW. FIG. 11B is a chart showing insecticidal protein bioassay LC-50 dose response results using three different insecticidal proteins (IP1-3) using the automated assay system, including larval mortality 6 days after infest for FAW. Proportion mortality for each replicate dose is shown.

FIG. 12: Larval growth inhibition (EC-50), mortality (LC-50) and time to mortality (LT-50) for five proteins against CEW. All values in ppm (diet+sample), except LT-50, which is in days.

DETAILED DESCRIPTION

Figure 1:
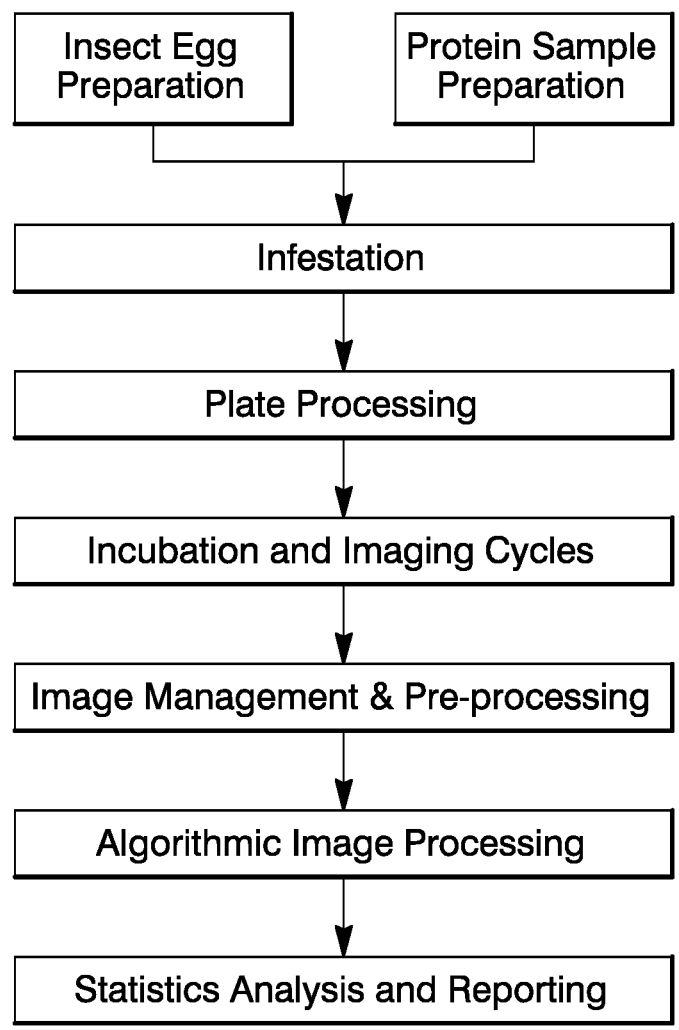
FIG. 1: Overall process flow chart for embodiments of automatic insect bioassays.

The embodiments of the invention are not limited by the exemplary methods and materials disclosed, and any methods and materials similar or equivalent to those described can be used in the practice or testing of embodiments of this invention. Numeric ranges are inclusive of the numbers defining the range.

The articles "a" and "an" are used to refer to one or more than one (i.e., to at least one) of the grammatical object of the article. For example, "an element" means one or more elements.

As used herein "high hatch rate" is intended to mean a hatch rate of insect eggs of at least 50%, at least 60%, at least 70%, at least 80%, at least 90%, or at least 100%.

As used herein, "insect" refers to all life stages of an insect or any one life stage of an insect, including but not limited to, eggs and larvae.

As used herein, "IC-50" or inhibition concentration, and "EC-50" or effective concentration each may be used interchangeably, and refers to the concentration at which the larvae size (as may be determined by the larvae pixel area) is half way between the maximum size (the zero dose control), and the smallest size (the most toxic dose). (See Ritz (2010) Environmental Toxicology and Chemistry 29:220-229, Ali and Luttrell (2009) Journal of Economic Entomology 102:1935-1947, Brvault et al. (2009), Journal of Economic Entomology 102:2301-2309, Kerr and Meador (1996), Environmental Toxicology and Chemistry 15:395-401, Marcon et al (1999) Journal of Economic Entomology 92:279-229).

As used herein, removing insect clumps includes, but is not limited to, clearing, dissolving, disintegrating, manually or mechanically separating clumping, aggergations or clustering of insects. Insect clumps may comprise insect eggs and/or insect larvae. In one embodiment, removing insect clumps comprises using a sieve. In another embodiment, removing insect clumps comprises using enzymatic or chemical breakdown of proteins holding the insects together, for example digesting peptides holding eggs together.

In one embodiment of the invention, a method is provided for sorting insects having a high hatch rate comprising rinsing insects with a rinse solution; discarding floating insects from the rinse solution; sterilizing the insects; separating immature insects from mature insects; and sorting the mature insects in using a sorting system. In another embodiment, a method is provided for sorting insects having a high hatch rate comprising removing insect clumps after incubating the insect eggs; incubating the insects until the insects show signs of development; and sorting the mature insects using a sorting system. In another embodiment, insects that are not viable or insect eggs that are not likely to hatch are discarded.

In some embodiments, the methods are useful using insects selected from the orders Coleoptera, Diptera, Hymenoptera, Lepidoptera, Mallophaga, Homoptera, Hemiptera Orthroptera, Thysanoptera, Dermaptera, Isoptera, Anoplura, Siphonaptera, Trichoptera, etc., particularly Lepidoptera and Coleoptera.

Larvae of the order Lepidoptera include, but are not limited to, armyworms, cutworms, loopers and heliothines in the family Noctuidae: *Spodoptera frugiperda* J E Smith (fall armyworm); *S. exigua* Hübner (beet armyworm); *S. litura* Fabricius (tobacco cutworm, cluster caterpillar); *Mamestra configurata* Walker (bertha armyworm); *M. brassicae* Linnaeus (cabbage moth); *Agrotis ipsilon* Hufnagel (black cutworm); *A. orthogonia* Morrison (western cutworm); *A. subterranea* Fabricius (granulate cutworm); *Alabama argillacea* Hübner (cotton leaf worm); *Trichoplusia ni* Hübner (cabbage looper); *Pseudoplusia includens* Walker (soybean looper); *Anticarsia gemmatalis* Hübner (velvetbean caterpillar); *Hypena scabra* Fabricius (green cloverworm); *Heliothis virescens* Fabricius (tobacco budworm); *Pseudaletia unipuncta* Haworth (armyworm); *Athetis mindara* Barnes and Mcdunnough (rough skinned cutworm); *Euxoa messoria* Harris (darksided cutworm); *Earias insulana* Boisduval (spiny bollworm); *E. vittella* Fabricius (spotted bollworm); *Helicoverpa armigera* Hübner (American bollworm); *H. zea* Boddie (corn earworm or cotton bollworm); *Melanchra picta* Harris (zebra caterpillar); *Egira* (*Xylomyges*) *curialis* Grote (citrus cutworm); borers, casebearers, webworms, coneworms, and skeletonizers from the family Pyralidae *Ostrinia nubilalis* Hübner (European corn borer); *Amyelois transitella* Walker (naval orangeworm); *Anagasta kuehniella* Zeller (Mediterranean flour moth); *Cadra cautella* Walker (almond moth); *Chilo suppressalis* Walker (rice stem borer); *C. partellus*, (sorghum borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenée (rice leaf roller); *Desmia funeralis* Hübner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Eoreuma loftini* Dyar (Mexican rice borer); *Ephestia elutella* Hübner (tobacco (cacao) moth); *Galleria mellonella* Linnaeus (greater wax moth); *Herpetogramma licarsisalis* Walker (sod webworm); *Homoeosoma electellum* Hulst (sunflower moth); *Elasmopalpus lignosellus* Zeller (lesser cornstalk borer); *Achroia grisella* Fabricius (lesser wax moth); *Loxostege sticticalis* Linnaeus (beet webworm); *Orthaga thyrisalis* Walker (tea tree web moth); *Maruca testulalis* Geyer (bean pod borer); *Plodia interpunctella* Hübner (Indian meal moth); *Scirpophaga incertulas* Walker (yellow stem borer); *Udea rubigalis* Guenée (celery leaftier); and leafrollers, budworms, seed worms and fruit worms in the family Tortricidae *Acleris gloverana* Walsingham (Western blackheaded budworm); *A. variana* Fernald (Eastern blackheaded budworm); *Archips argyrospila* Walker (fruit tree leaf roller); *A. rosana* Linnaeus (European leaf roller); and other *Archips* species, *Adoxophyes orana* Fischer von Rösslerstamm (summer fruit tortrix moth); *Cochylis hospes* Walsingham (banded sunflower moth); *Cydia latiferreana* Walsingham (filbertworm); *C. pomonella* Linnaeus (coding moth); *Platynota flavedana* Clemens (variegated leafroller); *P. stultana* Walsingham (omnivorous leafroller); *Lobesia botrana* Denis & Schiffermüller (European grape vine moth); *Spilonota ocellana* Denis & Schiffermilller (eyespotted bud moth); *Endopiza viteana* Clemens (grape berry moth); *Eupoecilia ambiguella* Hübner (vine moth); *Bonagota salubricola* Meyrick (Brazilian apple leafroller); *Grapholita molesta* Busck (oriental fruit moth); *Suleima helianthana* Riley (sunflower bud moth); *Argyrotaenia* spp.; *Choristoneura* spp.

Selected other agronomic insects in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Méneville (Chinese Oak Tussah Moth); *Bombyx mori* Linnaeus (Silkworm); *Bucculatrix thurberiella* Busck (cotton leaf perforator); *Colias eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Euproctis chrysorrhoea* Linnaeus (browntail moth); *Harrisina americana* Guérin-Méneville (grapeleaf skeletonizer); *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); Lymantria dispar Linnaeus (gypsy moth); *Manduca quinquemaculata* Haworth (five spotted hawk moth, tomato hornworm); *M. sexta* Haworth (tomato hornworm, tobacco hornworm); *Operophtera brumata* Linnaeus (winter moth); *Paleacrita vernata* Peck (spring cankerworm); *Papilio cresphontes* Cramer (giant swallowtail orange dog); *Phryganidia cahfornica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval and Leconte (Southern cabbageworm); *Sabulodes aegrotata* Guenée (omnivorous looper); *Schizura concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer); *Yponomeuta padella* Linnaeus (ermine moth); *Heliothis subflexa* Guenee; *Malacosoma* spp. and *Orgyia* spp.

Of interest are larvae and adults of the order Coleoptera including weevils from the families Anthribidae, Bruchidae and Curculionidae (including, but not limited to: *Anthonomus grandis* Boheman (boll weevil); *Lissorhoptrus oryzophilus* Kuschel (rice water weevil); *Sitophilus granarius* Linnaeus (granary weevil); *S. oryzae* Linnaeus (rice weevil); *Hypera punctata* Fabricius (clover leaf weevil); *Cylindrocopturus adspersus* LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug)); flea beetles, cucumber beetles, rootworms, leaf beetles, potato beetles and leafminers in the family Chrysomelidae (including, but not limited to: *Leptinotarsa decemlineata* Say (Colorado potato beetle); *Diabrotica virgifera virgifera* LeConte (western corn rootworm); *D. barberi* Smith and Lawrence (northern corn rootworm); *D. undecimpunctata howardi* Barber (southern corn rootworm); *Chaetocnema pulicaria* Melsheimer (corn flea beetle); *Phyllotreta cruciferae* Goeze (Crucifer flea beetle); *Phyllotreta striolata* (stripped flea beetle); *Colaspis brunnea* Fabricius (grape colaspis);

*Oulema melanopus* Linnaeus (cereal leaf beetle); *Zygogramma exclamationis* Fabricius (sunflower beetle)); beetles from the family Coccinellidae (including, but not limited to: *Epilachna varivestis* Mulsant (Mexican bean beetle)); chafers and other beetles from the family Scarabaeidae (including, but not limited to: *Popillia japonica* Newman (Japanese beetle); *Cyclocephala borealis* Arrow (northern masked chafer, white grub); *C. immaculata* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle)); carpet beetles from the family Dermestidae; wireworms from the family Elateridae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebrionidae.

Adults and immatures of the order Diptera are of interest, including leafminers *Agromyza parvicornis* Loew (corn blotch leafminer); midges (including, but not limited to: *Contarinia sorghicola* Coquillett (sorghum midge); *Mayetiola destructor* Say (Hessian fly); *Sitodiplosis mosellana* Galin (wheat midge); *Neolasioptera murtfeldtiana* Felt, (sunflower seed midge)); fruit flies (Tephritidae), *Oscinella frit* Linnaeus (fruit flies); maggots (including, but not limited to: *Delia platura* Meigen (seedcorn maggot); *D. coarctata* Fallen (wheat bulb fly) and other *Delia* spp., *Meromyza americana* Fitch (wheat stem maggot); *Musca domestica* Linnaeus (house flies); *Fannia canicularis* Linnaeus, *F. femoralis* Stein (lesser house flies); *Stomoxys calcitrans* Linnaeus (stable flies)); face flies, horn flies, blow flies, *Chrysomya* spp.; *Phormia* spp. and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds) and other *Brachycera*, mosquitoes *Aedes* spp.; *Anopheles* spp.; *Culex* spp.; black flies *Prosimulium* spp.; *Simulium* spp.; biting midges, sand flies, sciarids, and other *Nematocera*.

Included as insects of interest are adults and nymphs of the orders Hemiptera and Homoptera such as, but not limited to, adelgids from the family Adelgidae, plant bugs from the family Miridae, cicadas from the family Cicadidae, leafhoppers, *Empoasca* spp.; from the family Cicadellidae, planthoppers from the families Cixiidae, Flatidae, Fulgoroidea, Issidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Asterolecanidae, Coccidae, Dactylopiidae, Diaspididae, Eriococcidae Ortheziidae, Phoenicococcidae and Margarodidae, lace bugs from the family Tingidae, stink bugs from the family Pentatomidae, cinch bugs, *Blissus* spp.; and other seed bugs from the family Lygaeidae, spittlebugs from the family Cercopidae squash bugs from the family Coreidae and red bugs and cotton stainers from the family Pyrrhocoridae.

Agronomically important members from the order Homoptera further include, but not limited to: *Acyrthisiphon pisum* Harris (pea aphid); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacorthum solani* Kaltenbach (foxglove aphid); *Chaetosiphon fragaefolii* Cockerell (strawberry aphid); *Diuraphis noxia* Kurdjumov/Mordvilko (Russian wheat aphid); *Dysaphis plantaginea* Paaserini (rosy apple aphid); *Eriosoma lanigerum* Hausmann (woolly apple aphid); *Brevicoryne brassicae* Linnaeus (cabbage aphid); *Hyalopterus pruni* Geoffroy (mealy plum aphid); *Lipaphis erysimi* Kaltenbach (turnip aphid); *Metopolophium dirrhodum* Walker (cereal aphid); *Macrosiphum euphorbiae* Thomas (potato aphid); *Myzus persicae* Sulzer (peach-potato aphid, green peach aphid); *Nasonovia ribisnigri* Mosley (lettuce aphid); *Pemphigus* spp. (root aphids and gall aphids); *Rhopalosiphum maidis* Fitch (corn leaf aphid); *R. padi* Linnaeus (bird cherry-oat aphid); *Schizaphis graminum* Rondani (greenbug); *Sipha flava* Forbes (yellow sugarcane aphid); *Sitobion avenae* Fabricius (English grain aphid); *Therioaphis maculata* Buckton (spotted alfalfa aphid); *Toxoptera aurantii* Boyer de Fonscolombe (black citrus aphid) and *T. citricida* Kirkaldy (brown citrus aphid); *Melanaphis sacchari* (sugarcane aphid); *Adelges* spp. (adelgids); *Phylloxera devastatrix* Pergande (pecan phylloxera); *Bemisia tabaci* Gennadius (tobacco whitefly, sweetpotato whitefly); *B. argentifolii* Bellows & Perring (silverleaf whitefly); *Dialeurodes citri* Ashmead (citrus whitefly); *Trialeurodes abutiloneus* (bandedwinged whitefly) and *T. vaporariorum* Westwood (greenhouse whitefly); *Empoasca fabae* Harris (potato leafhopper); *Laodelphax striatellus* Fallen (smaller brown planthopper); *Macrolestes quadrilineatus* Forbes (aster leafhopper); *Nephotettix cinticeps* Uhler (green leafhopper); *N. nigropictus* stål (rice leafhopper); *Nilaparvata lugens* stål (brown planthopper); *Peregrinus maidis* Ashmead (corn planthopper); *Sogatella furcifera* Horvath (white-backed planthopper); *Sogatodes orizicola* Muir (rice delphacid); *Typhlocyba pomaria* McAtee (white apple leafhopper); *Erythroneoura* spp. (grape leafhoppers); *Magicicada septendecim* Linnaeus (periodical cicada); *Icerya purchasi* Maskell (cottony cushion scale); *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla); *Trioza diospyri* Ashmead (persimmon psylla).

Agronomically important species of interest from the order Hemiptera include, but are not limited to: *Acrosternum hilare* Say (green stink bug); *Anasa tristis* De Geer (squash bug); *Blissus leucopterus leucopterus* Say (chinch bug); *Corythuca gossypii* Fabricius (cotton lace bug); *Cyrtopeltis modesta* Distant (tomato bug); *Dysdercus suturellus* Herrich-Schäffer (cotton stainer); *Euschistus servus* Say (brown stink bug); *E. variolarius* Palisot de Beauvois (one-spotted stink bug); *Graptostethus* spp. (complex of seed bugs); *Leptoglossus corculus* Say (leaf-footed pine seed bug); *Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Lygocoris pabulinus* Linnaeus (common green capsid); *Nezara viridula* Linnaeus (southern green stink bug); *Oebalus pugnax* Fabricius (rice stink bug); *Oncopeltus fasciatus* Dallas (large milkweed bug); *Pseudatomoscelis seriatus* Reuter (cotton fleahopper).

Furthermore, embodiments may be effective using Hemiptera such as, *Calocoris norvegicus* Gmelin (strawberry bug); *Orthops campestris* Linnaeus; *Plesiocoris rugicollis* Fallen (apple capsid); *Cyrtopeltis modestus* Distant (tomato bug); *Cyrtopeltis notatus* Distant (suckfly); *Spanagonicus albofasciatus* Reuter (whitemarked fleahopper); *Diaphnocoris chlorionis* Say (honeylocust plant bug); *Labopidicola allii* Knight (onion plant bug); *Pseudatomoscelis seriatus* Reuter (cotton fleahopper); *Adelphocoris rapidus* Say (rapid plant bug); *Poecilocapsus lineatus* Fabricius (four-lined plant bug); *Nysius ericae* Schilling (false chinch bug); *Nysius raphanus* Howard (false chinch bug); *Nezara*

*viridula* Linnaeus (Southern green stink bug); *Eurygaster* spp.; *Coreidae* spp.; *Pyrrhocoridae* spp.; *Tinidae* spp.; *Blostomatidae* spp.; *Reduviidae* spp. and *Cimicidae* spp.

Also included are adults and larvae of the order Acari (mites) such as *Aceria tosichella* Keifer (wheat curl mite); *Petrobia latens* Müller (brown wheat mite); spider mites and red mites in the family Tetranychidae, *Panonychus ulmi* Koch (European red mite); *Tetranychus urticae* Koch (two spotted spider mite); (*T. mcdanieli* McGregor (McDaniel mite); *T. cinnabarinus* Boisduval (carmine spider mite); *T. turkestani* Ugarov & Nikolski (strawberry spider mite); flat mites in the family Tenuipalpidae, *Brevipalpus lewisi* McGregor (citrus flat mite); rust and bud mites in the family Eriophyidae and other foliar feeding mites and mites important in human and animal health, i.e., dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick) and scab and itch mites in the families Psoroptidae, Pyemotidae and Sarcoptidae.

Insect pests of the order Thysanura are of interest, such as *Lepisma saccharina* Linnaeus (silverfish); *Thermobia domestica* Packard (firebrat).

Additional arthropod insects covered include: spiders in the order Araneae such as *Loxosceles reclusa* Gertsch and Mulaik (brown recluse spider) and the *Latrodectus mactans* Fabricius (black widow spider) and centipedes in the order Scutigeromorpha such as *Scutigera coleoptrata* Linnaeus (house centipede).

Insects of interest include the superfamily of stink bugs and other related insects including but not limited to species belonging to the family Pentatomidae (*Nezara viridula, Halyomorpha halys, Piezodorus guildini, Euschistus servus, Acrosternum hilare, Euschistus heros, Euschistus tristigmus, Acrosternum hilare, Dichelops furcatus, Dichelops melacanthus,* and *Bagrada hilaris* (Bagrada Bug)), the family Plataspidae (*Megacopta cribraria*—Bean plataspid) and the family Cydnidae (*Scaptocoris castanea*—Root stink bug) and Lepidoptera species including but not limited to: diamond-back moth, e.g., *Helicoverpa zea* Boddie; soybean looper, e.g., *Pseudoplusia includens* Walker and velvet bean caterpillar e.g., *Anticarsia gemmatalis* Hübner.

Nematodes include parasitic nematodes such as root-knot, cyst and lesion nematodes, including *Heterodera* spp., *Meloidogyne* spp. and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode) and *Globodera rostochiensis* and *Globodera pailida* (potato cyst nematodes). Lesion nematodes include *Pratylenchus* spp. As used herein, "insects" does not include nematodes.

Methods for measuring pesticidal activity are well known in the art. See, for example, Czapla and Lang, (1990) *J. Econ. Entomol.* 83:2480-2485; Andrews, et al., (1988) *Biochem. J.* 252:199-206; Marrone, et al., (1985) *J. of Economic Entomology* 78:290-293 and U.S. Pat. No. 5,743,477, all of which are herein incorporated by reference in their entirety. Generally, the protein is mixed and used in feeding assays. See, for example Marrone, et al., (1985) *J. of Economic Entomology* 78:290-293. Such assays can include contacting a food source with one or more insects and determining the insect's ability to survive.

Methods are provided for sorting insects. In some embodiments, methods are provided for sorting insects having a high hatch rate comprising rinsing insects with a rinse solution; discarding floating insects from the rinse solution; sterilizing the insects; separating immature insects from mature insects; and sorting the mature insects using a sorting system. In another embodiment, a method is provided for sorting insects having a high hatch rate comprising removing insect clumps; incubating the insects until the insects show signs of development; and sorting the mature insects using sorting system.

In another embodiment, methods are provided for assaying insects. In some embodiments, methods are provided for assaying insects comprising placing an insect into a well of an assay plate; capturing an image of the well of the assay plate; and determining a metric measurement of the insect in the well of the assay plate. In one embodiment, the metric measurement of the insect comprises the use of the pixel count of the image.

Another embodiment relates to a method for preparing insects for a bioassay. In some embodiments, methods are provided for preparing insects for bioassay comprising preparing individually dispersed insects; and dispensing a predetermined number of individually dispersed insects into each well of an assay plate.

Methods are provided for assaying the activity of insecticidal compounds using an automated system. In some embodiments, methods are provided relating to assaying the activity of insecticidal compounds using an automated system comprising providing a multi-well plate with at least one insect in a predetermined number of wells of a multi-well plate; transporting by automated means the multi-well plate to an incubation device for incubation of the multi-well plate; and transporting by automated means the multi-well plate to a measuring device for measuring movement or determining a metric measurement.

Methods are provided for sorting insect eggs. In some embodiments, methods are provided for sorting insect eggs having a high hatch rate comprising rinsing insect eggs with a rinse solution; discarding floating insect eggs from the rinse solution; sterilizing the insect eggs; separating immature insect eggs from mature insect eggs; and sorting the mature insect eggs using a sorting system. In another embodiment, a method is provided for sorting insect eggs having a high hatch rate comprising removing insect eggs clumps; incubating the insect eggs until the insect eggs show signs of development; and sorting the mature insect eggs using sorting system.

In another embodiment, methods are provided for assaying insects. In some embodiments, methods are provided for assaying insects comprising placing an insect egg into a well of an assay plate; capturing an image of the well of the assay plate; and determining a metric measurement of the insect in the well of the assay plate. In one embodiment, the metric measurement of the insect comprises the use of the pixel count of the image.

Another embodiment relates to a method for preparing insect eggs for a bioassay. In some embodiments, methods are provided for preparing insect eggs for bioassay comprising preparing individually dispersed insect eggs; selecting insect eggs which are ready to hatch within a predetermined time frame; and dispensing a pre-determined number of individually dispersed insect eggs into each well of an assay plate.

Methods are provided for assaying the activity of insecticidal compounds using an automated system. In some embodiments, methods are provided relating to assaying the activity of insecticidal compounds using an automated system comprising providing a multi-well plate with at least one insect eggs in a predetermined number of wells of a multi-well plate; transporting by automated means the multi-well plate to an incubation device for incubation of the multi-well plate; and transporting by automated means the multi-well plate to a measuring device for measuring movement or determining a metric measurement.

In one embodiment, the method of sorting insects comprises sorting insect eggs. In another embodiment, the method of sorting insects comprises sorting insect larvae. In a further embodiment, the method of sorting insects relates to a method of sorting insect eggs and larvae.

In one embodiment, a method relating to sorting insects comprises selecting a mature insect egg. A mature insect egg is an insect egg that has a high probability of hatching within a predetermined time frame. In one embodiment, selecting a mature insect egg comprises pretreating an insect. In a further embodiment, the insect egg is sorted by density gradient sorting and/or by a sorting system 1 (or a plurality of sorting systems) as further disclosed herein.

In one embodiment, the sorting system 1 may be capable of sorting using fluorescence, size, optical density, and side scatter parameters. In exemplary embodiments, and with reference to FIGS. 13-16, the sorting system 1 can comprise a large particle sorting system (e.g., a large particle flow cytometer) as is known in the art. In use, such large particle sorting systems can provide for automated analysis and sorting of insect eggs and insects as further disclosed herein. For example, the large particle sorting system can be capable of sorting objects by length, optical density, and fluorescence. In exemplary configurations, the large particle sorting system can comprise a reservoir pressurized to produce a constant flow rate of fluid through a flow channel. The sample can be contained within a continuously mixing sample container and be sufficiently pressurized to penetrate a laminar sheath stream, resulting in a core sample stream carried by the surrounding reservoir flow and centered in the flow stream where it, can be illuminated by at least one visible laser (optionally, a plurality of lasers). The large particle sorting system can further comprise sensors or detectors that measure various parameters, such as time of flight (length of signal), optical density, and fluorescence emissions, which can be analyzed as optical characteristics that can be used as sort criteria. As fluid exits the flow channel, it can be diverted by an air stream to a recovery container. Alternatively, during a sorting operation, the air stream will be turned off (to prevent diverting of the fluid), and droplets of the fluid containing the sortable object can be dispensed by a nozzle. In further embodiments, the sorting system can comprise a stage that is configured to support a multi-well plate that receives droplets from the dispensing nozzle. Objects that were diverted into the recovery container can be retrieved as desired for further assessment and analysis. As further disclosed herein, the sorting system can further comprise a computer 120 that is configured to control operation of the sorting system and that can be loaded with software for conducting data processing and sorting operations. In use, the large particle sorting system can be coupled to a large particle sampling assembly, as is known in the art, which can present samples to the large particle sorting system. One example of a large particle sorting system that is suitable for use as a sorting system as disclosed herein is a COPAS® (Union Biometrica, Inc., Holliston, MA) platform sorting system. In one embodiment, the sorting system selects eggs that are likely to hatch based on a combination of pre-optimized ranges of green fluorescence, red fluorescence and/or side-scatter readings.

In a specific embodiment, the rinse solution comprises a bleach solution, an acidic, and/or an alcohol solution. In one embodiment the rinse solution is a peracetic acid solution. In one embodiment, the rinse solution is an ethanol solution. In another embodiment, a rinsing may occur sequentially, with each rinse comprising a different rinse solution or the same rinse solution.

In another embodiment, the method further includes the step of infesting insects into an assay plate. In another embodiment, the insects are sorted prior to infesting an assay plate. In a further embodiment, the insects are infested using the sorting system 1 to infest the assay plates. In this embodiment, the sorting system 1 can be a large particle sorting system that ejects insects into corresponding wells of the assay plates. An assay plate comprises at least 2, at least 4, at least 6, at least 8, at least 12, at least 24, at least 48, at least 96, or at least 384 wells. In one embodiment, an assay plate may be a microtiter plate. In one embodiment, the method relates to infesting one insect per well. In another embodiment, the method relates to infesting more than one insect per well. In one embodiment, the method relates to infesting a predetermined number of insects equally into a plurality of wells. In another embodiment, the well contains a food source. In one embodiment, the assay plates contain artificial diet food source. In a further embodiment, the artificial diet food source is dyed to prevent or adjust emitted fluorescence from a well in an assay plate. In a further embodiment, a well contains an insecticidal source. In one embodiment the insecticidal source comprises at least one of the group consisting of an insecticidal protein, an insecticidal silencing element or double stranded RNA, or an insecticidal chemistry.

In one embodiment, the method comprises the automated infesting of insects into an assay plate. In another embodiment, the automated infesting comprises the use of a robotic arm to move the assay plates into the proper position for infesting, drying diet, sealing the assay plates, or punching holes in the sealed assay plates. In this embodiment, the robotic arm 10 can be a component of a larger robot assembly, which can comprise processing circuitry positioned in communication with other system components as further disclosed herein. It is contemplated that the robotic arm 10 can comprise an end effector that is configured to selectively engage, orient, position, and disengage an assay plate as further disclosed herein. Optionally, the end effector can comprise a gripper, such as, for example and without limitation, an impactive gripper (e.g., at least one claw or jaw), an astrictive gripper (e.g., a suction apparatus), a contigutive gripper (e.g., a gripper having a surface that comprises glue or is capable of applying surface tension or freezing action), or combinations thereof, It is further contemplated that the robotic arm 10 can comprise a plurality of links that are coupled together at joints that allow for rotational motion or axial translation of links relative to one another. Optionally, it is contemplated that the robotic arm 10 can be a multi-axis robotic arm having multiple degrees of freedom. For example, it is contemplated that the multi-axis robotic arm can be configured for axial movement in a plurality of axes and rotational movement in at least one axis (optionally, a plurality of axes).

In one embodiment, the assay plates comprise a barcode. In this embodiment, it is contemplated that the system can further comprise at least one barcode reader as is known in the art, which can be communicatively coupled to a computer or other processing equipment as further disclosed herein. In one embodiment the assay plate is a white, clear, opaque, black or other colored assay plate.

In another embodiment, a method is provided for assaying insects comprising placing an insect into a well of an assay plate; capturing an image of the well of the assay plate; and determining a measurement of the insect in the well of the assay plate. In this embodiment, the placement of an insect into a well of an assay plate can be performed using a sorting system as further disclosed herein. It is further contemplated that the image of the well of the assay plate can be recorded using an imaging system, which can comprise at least one imaging assembly 7. Optionally, the imaging system can comprise a camera, a microscope, x-ray equipment, magnetic resonance imaging (MRI) equipment, laser three-dimensional ("3-D") scanners, and various other equipment configured to produce images and identify shapes, patterns, orientation, colors, and or other characteristics of objects. In one embodiment, the measurement of the insect comprises the use of the pixel count of the image recorded by the imaging system. In another embodiment, the measurement comprises the fluorescence of an insect in a well of an assay plate. In one embodiment, the measurement comprises detecting and/or recording the movement of an insect in a well in of an assay plate. Optionally, in this embodiment, the movement of the insect can be detected by a machine vision device. Machine vision, as used herein, refers to apparatuses and methods which use electronic sensory equipment to electronically identify shapes, colors, patterns, orientation, and/or other characteristics of objects. In this regard, the machine vision device will generally be described herein as being camera-based for purposes of brevity. However, the machine vision device may in some embodiments comprise x-ray equipment, magnetic resonance imaging (MRI) equipment; laser three-dimensional ("3-D") scanners, and various other equipment configured to identify shapes, patterns, orientation, colors, and or other characteristics of objects. Accordingly, the machine vision device, either alone or in combination with processing equipment described herein, may be used to detect movement of an insect as disclosed herein. Optionally, the movement of the insect can be detected using the imaging system (i.e., at least one imaging assembly 7) as disclosed herein. Thus, it is contemplated that the imaging system can comprise at least one camera that is capable of recording an image and, using processing circuitry as disclosed herein, detecting movement as disclosed herein. Additionally, or alternatively, the movement of an insect can be detected and/or recorded using a motion sensor or detector as is known in the art.

In a further embodiment, the detecting and/or recording the movement comprises aligning two or more images from a time interval of an insect in a well of an assay plate. In this embodiment, the two or more images can be aligned using imaging software stored on an imaging computer 130, 132 as further disclosed herein. For example, such imaging software can be configured to produce an output corresponding to a visual overlay of discrete images, taken at various times during the time interval, with such output being presented on a display device positioned in communication with a processor of the imaging computer. In use, it is contemplated that the displayed output can create a reference value that can be used to measure changes in movement (or area) over time. In another embodiment, the measurement comprises a metric measurement. In this embodiment, it is contemplated that the metric measurement can be determined using imaging software stored on a computer as further disclosed herein, with the imaging software being configured to determine the size (e.g., body area) of an insect or a portion of an insect by processing a previously captured image of the insect. In exemplary embodiments, the body area measurement can be recorded in combination with other metrics (e.g., length, width, position, light intensity, size differential between time intervals). Additionally, or alternatively, the metric measurement can be determined using a non-contact sensor that is capable of measuring size parameters (e.g, area, distance, length, etc.). Examples of such sensors include optical or laser sensors, gauges, or encoders as are known in the art. However, it is contemplated that any known non-contact measurement sensor can be used. In use, area and position measurements can be used to generate insect response statistics, with the other disclosed measurements being used to evaluate and determine insect response. In one embodiment, a method comprising placing an insect into a well of an assay plate; capturing an image of the well of the assay plate; and determining a measurement of the insect in the well of the assay plate is repeated for each well in an assay plate.

In another embodiment, a method relates to a bioassay comprising sorting an insect and determining an IC-50, EC-50 or an LC-50. In a further embodiment, a method relates to a bioassay comprising sorting an insect (e.g., using a sorting system as disclosed herein), capturing an image of an insect (e.g., using a camera of an imaging system as disclosed herein), and determining an IC-50, EC-50 or an LC-50. In one embodiment, an IC-50, or EC-50 is determined by a size metric measurement of an insect, which can be performed using imaging software or a sensor as disclosed herein. In one embodiment, an LC-50 is determined by a measurement of movement of an insect.

In one embodiment, the method relates to determining the toxicity or insecticidal activity of a test substance, such as an insecticidal protein, an insecticidal silencing element or double stranded RNA, or a non-protein insecticidal chemical. In one embodiment, the test substance is a new variant, a shuffled variant, or a domain swapped insecticidal protein. In another embodiment, the test protein is an unknown protein or a protein of unknown toxicity or insecticidal activity to insects. In a further embodiment, the assay comprises the use of a positive control insecticidal protein, wherein the toxicity of the positive control insecticidal protein is known. In one embodiment, the toxicity of a test protein is determined by determining an IC-50, EC-50 or an LC-50 of the test protein.

In one embodiment, and with reference to FIGS. 13-16, an automated insect bioassay system can comprise at least one sorting system 1 (optionally, a plurality of sorting systems, such as first, second, and third sorting systems 1, 21, 22) as further disclosed herein. Optionally, the bioassay system can further comprise at least one robotic arm 10 (optionally, a plurality of robotic arms 15, 16) as further disclosed herein. Each robotic arm 10, 15, 16 can have its own processing circuitry, which can be configured to control operation of the robotic arm and other system components as disclosed herein. Optionally, the processing circuitry of the robotic arm can comprise a central control (master) computer 11, 101 as disclosed herein.

Each sorting system 1, 21, 22 can have its own processing circuitry (e.g., a computer 120, 122, 124 as disclosed herein) that is configured to permit selective control of the operation of the sorting system. In use, the processing circuitry of each sorting system can be communicatively coupled (e.g., integrally connected or wirelessly connected) to processing circuitry of a robotic arm using conventional mechanisms, such as ActiveX control and/or serial port connection.

In another embodiment, the bioassay system can further comprise a plate sealing assembly 3, such as, for example and without limitation, a PlateLoc Thermal Microplate Sealer manufactured by Agilent Technologies, Inc. In one embodiment, as is known in the art, the plate sealing assembly 3 can comprise a stage for receiving an assay plate, a support for a roll of sealing material, a dispensing apparatus for advancing and applying sealing material in a selected amount and at a selected rate, and a user interface that permits control of sealing parameters (e.g., temperature, seal time, etc.). In use, and as further described herein, it is contemplated that the plate sealing assembly 3 can comprise processing circuitry that is communicatively coupled (e.g., integrally connected or wirelessly connected) to processing circuitry of a robotic arm using conventional mechanisms, such as ActiveX control and/or serial port connection.

In another embodiment, the automated insect bioassay system can further comprise a piercing assembly 2, such as, for example and without limitation, a Microplate Seal Piercer manufactured by Agilent Technologies, Inc. As is known in the art, the piercing assembly 2 can comprise a stage for receiving an assay plate, a piercing head that is configured for cyclical movement to pierce particular (e.g., selected or predetermined) portions of a seal that has been previously applied over an assay plate, at least one actuator for effecting cyclical movement of the piercing head, and a user interface that is coupled to the actuator and that permits control of the piercing operation. Optionally, the piercing head can define a plurality of projections that are generally vertically aligned with respective wells of the assay plate during a piercing operation. In use, and as further disclosed herein, it is contemplated that the piercing assembly 2 can comprise processing circuitry that is communicatively coupled (e.g., integrally connected or wirelessly connected) to processing circuitry of a robotic arm using conventional mechanisms, such as ActiveX control and/or serial port connection.

In another embodiment, the automated insect bioassay system can further comprise at least one imaging assembly 7 (optionally, first and second imaging assemblies 7, 14) as disclosed herein. In this embodiment, the imaging assembly 7 can comprise a camera, a microscope, a sensor, or combinations thereof. The imaging assembly 7 can comprise a stage configured to receive and support an assay plate while a camera or microscope captures images of one or more wells of the assay plate. The imaging assembly 7 can be communicatively coupled to processing circuitry, which can permit selective control of the operation (e.g., activation and image acquisition parameters) of the imaging assembly. In use, the processing circuitry of the imaging assembly 7 can be communicatively coupled (e.g., integrally connected or wirelessly connected) to processing circuitry of a robotic arm using conventional mechanisms, such as ActiveX control and/or serial port connection.

In another embodiment, the automated insect bioassay system can comprise an evaporator 4, such as, for example and without limitation, an ULTRAVAP microplate evaporator manufactured by Porvair Sciences. As is known in the art, the evaporator 4 can comprise a stage that is configured to receive and support an assay plate, blow-down equipment (e.g., needles, pumps, nozzles, and the like) that is positioned above the stage and capable of accomplishing evaporation of liquid within respective wells of an assay plate, and processing circuitry that permits selective control of the operation (e.g., activation and drying parameters) of the evaporator 4. In use, the processing circuitry of the evaporator 4 can be communicatively coupled (e.g., integrally connected or wirelessly connected) to processing circuitry of a robotic arm using conventional mechanisms, such as ActiveX control and/or serial port connection.

In a further embodiment, the automated insect bioassay system can comprise at least one incubator 5 (optionally, a plurality of incubators, such as first and second incubators 5, 6), which can have a housing configured to receive at least one assay plate and equipment (e.g., heating sources, cooling sources, filters, fans, ventilation systems, sensors, and the like) that is configured to control various conditions within the housing (e.g., temperature, humidity, carbon dioxide content, oxygen content, and the like). In this embodiment, each incubator can further comprise processing circuitry that is communicatively coupled to the equipment that controls the various conditions within the housing. In use, the processing circuitry of each incubator 5, 6 can be communicatively coupled (e.g., integrally connected or wirelessly connected) to processing circuitry of a robotic arm using conventional mechanisms, such as ActiveX control and/or serial port connection.

In another embodiment, the automated insect bioassay system can comprise at least one plate storage assembly 8, such as, for example and without limitation, a Labware MiniHub manufactured by Agilent Technologies, Inc. In this embodiment, the plate storage assembly can comprise at least one support shaft and a plurality of receptacles mounted along the length of the support shaft for receiving and supporting respective assay plates (or other laboratory equipment). The plate storage assembly 8 can further comprise a rotational actuator configured to effect rotation of the plate storage assembly 8 and thereby provide access to selected assay plates that are stored on the plate storage assembly. The plate storage assembly 8 can further comprise processing circuitry that is communicatively coupled to the actuator to permit selective control of the rotational position of the plate storage assembly. Optionally, the automated insect bioassay system can comprise a plurality of plate storage assemblies, such as first and second storage assemblies 8, 17. In use, the processing circuitry of each plate storage assembly 8 can be communicatively coupled (e.g., integrally connected or wirelessly connected) to processing circuitry of a robotic arm using conventional mechanisms, such as ActiveX control and/or serial port connection.

In a further embodiment, the automated insect bioassay system can comprise at least one plate stacking assembly 9 (optionally, first and second plate stacking assemblies 23, 24), such as, for example and without limitation, a Labware Stacker manufactured by Agilent Technologies, Inc. In this embodiment, plate stacking assembly 9 can comprise a vertical receptacle that contains a plurality of racks that permit stacking and sequential dispensing of assay trays. Optionally, the plate stacking assembly 9 can further comprise an engagement apparatus (e.g., a gripper, a claw) that is configured to sequentially dispense individual assay trays from a stack of assay trays. The plate stacking assembly 9 can further comprise an unloading opening positioned in communication with the vertical receptacle to permit engagement between the robotic arm and a plate that is dispensed by the plate stacking assembly. In use, processing circuitry of the plate stacking assembly 9, which can be configured to permit selective control of the dispensing of plates, can be communicatively coupled (e.g., integrally connected or wirelessly conected) to processing circuitry of a robotic arm using conventional mechanisms, such as ActiveX control and/or serial port connection.

In a further embodiment, the automated insect bioassay system can comprise at least one bar code reader (e.g., first and second barcode readers 18, 19) that is positioned at selected locations within the system to permit tracking of the locations of individual plates (which have been previously barcoded as disclosed herein). Each bar code reader can comprise processing circuitry that is configured to transmit information concerning the detection and scanning of bar codes (e.g., time, location, plate identification and the like). Optionally, each bar code reader can be communicatively coupled to a robotic arm. Additionally, or alternatively, each bar code reader can be communicatively coupled to a master computer 11, 101 or remote computing device 114a, 114b, 114c as further disclosed herein.

As can be appreciated with reference to the examples depicted in FIGS. 13-16, it is possible to construct an automated insect bioassay system using components that are fully compatible with robot-implemented systems, with the processing circuitry of the robotic arm 10 (e.g., a control (master) computer 11, 101) communicating with all system components and serving as the central processing unit for the overall system. In this example, it is contemplated that the robotic arm 10 can be positioned centrally within the system, with the remaining system components positioned in a desired arrangement around the robotic arm. In one embodiment, the stages and other accessible areas of the system components can be positioned at an optimal radial position relative to the robotic arm to ensure that those areas of the system components can be easily accessed by the robotic arm when the robotic arm is radially deployed. It is contemplated that such configurations can permit fully automated system operation.

In the description of sorting operations provided herein, it is contemplated that all steps of the sorting process can be performed in an automated manner. Where specific structure for performing a step is not provided in the description, it is understood that such step can be performed by corresponding processing circuitry as disclosed herein, which can control operation of system components or conduct analysis in an automated manner.

In alternative embodiments, the methods and systems disclosed herein, in whole or in part, necessarily require implementation using a machine, computer system or equivalent, within which a set of instructions for causing the computer or machine to perform any one or more of the protocols or methodologies of the invention may be executed. In alternative embodiments, the machine may be connected (e.g., networked) to other machines, e.g., in a Local Area Network (LAN), an intranet, an extranet, or the Internet, or any equivalents thereof. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. The term "machine" shall also be taken to include any collection of machines, computers or products of manufacture that individually or jointly execute a set (or multiple sets) of instructions to perform any one or more of the methodologies of the invention.

Figure 17:
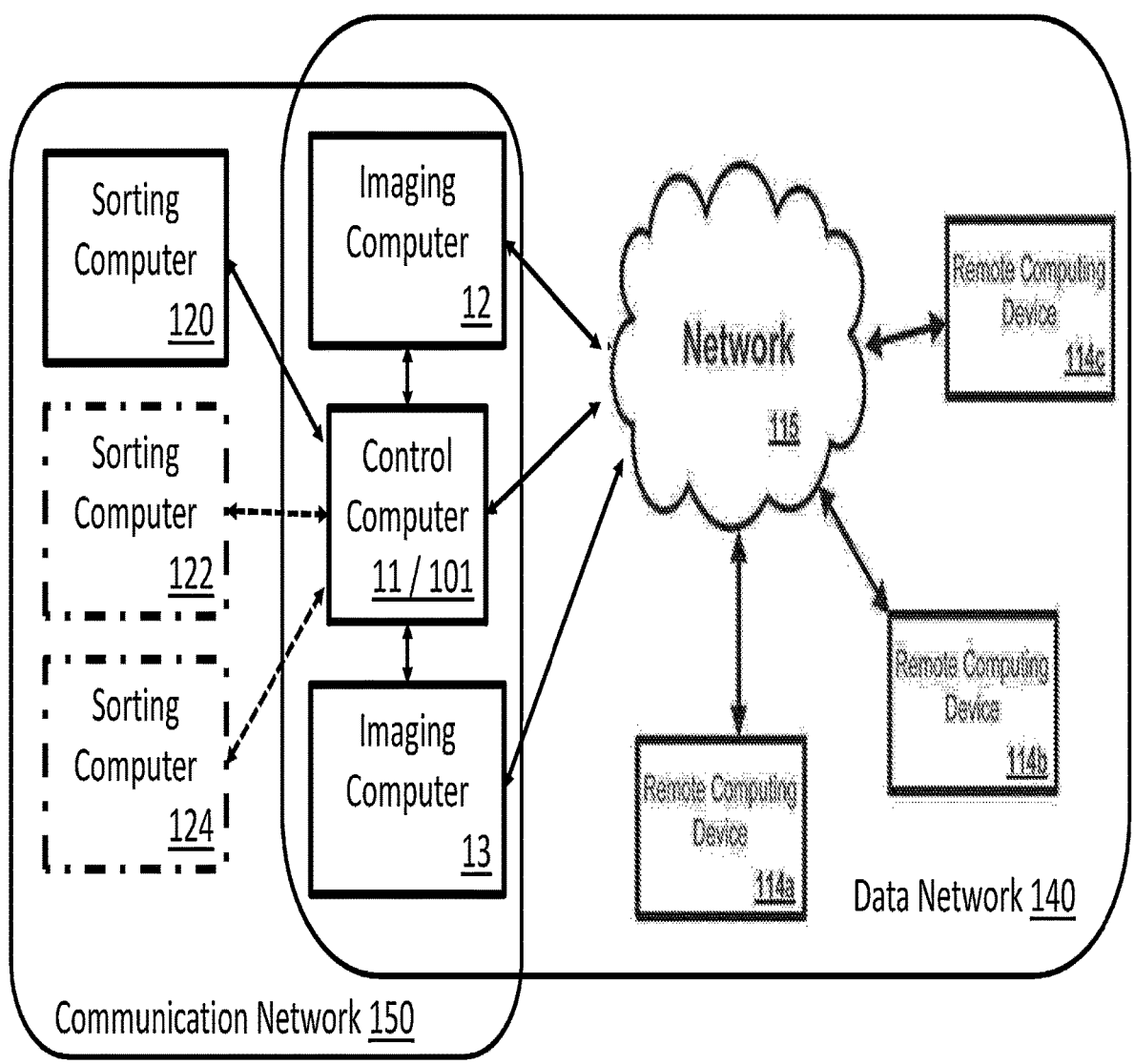
FIG. 17 is a schematic diagram depicting an exemplary arrangement of a computer system for use with an automated insect bioassay system as disclosed herein.

In alternative embodiments, and with reference to FIG. 17, an exemplary computer system of the invention comprises a data network 140 and a communication network 150. In exemplary embodiments, the data network 140 can comprise a control (master) computer 101 and at least one imaging computer (e.g., first and second imaging computers 12, 13), which can be communicatively coupled to the control computer. The communication network 150 can comprise computers 120, 122, 124 of the sorting systems 1, 21, 22 disclosed herein. In one embodiment, the sorting computers 120, 122, 124 can be communicatively coupled to the control computer 101 to communicate data obtained from the sorting systems and to permit control of the sorting system via instructions received from the control computer.

Figure 15:
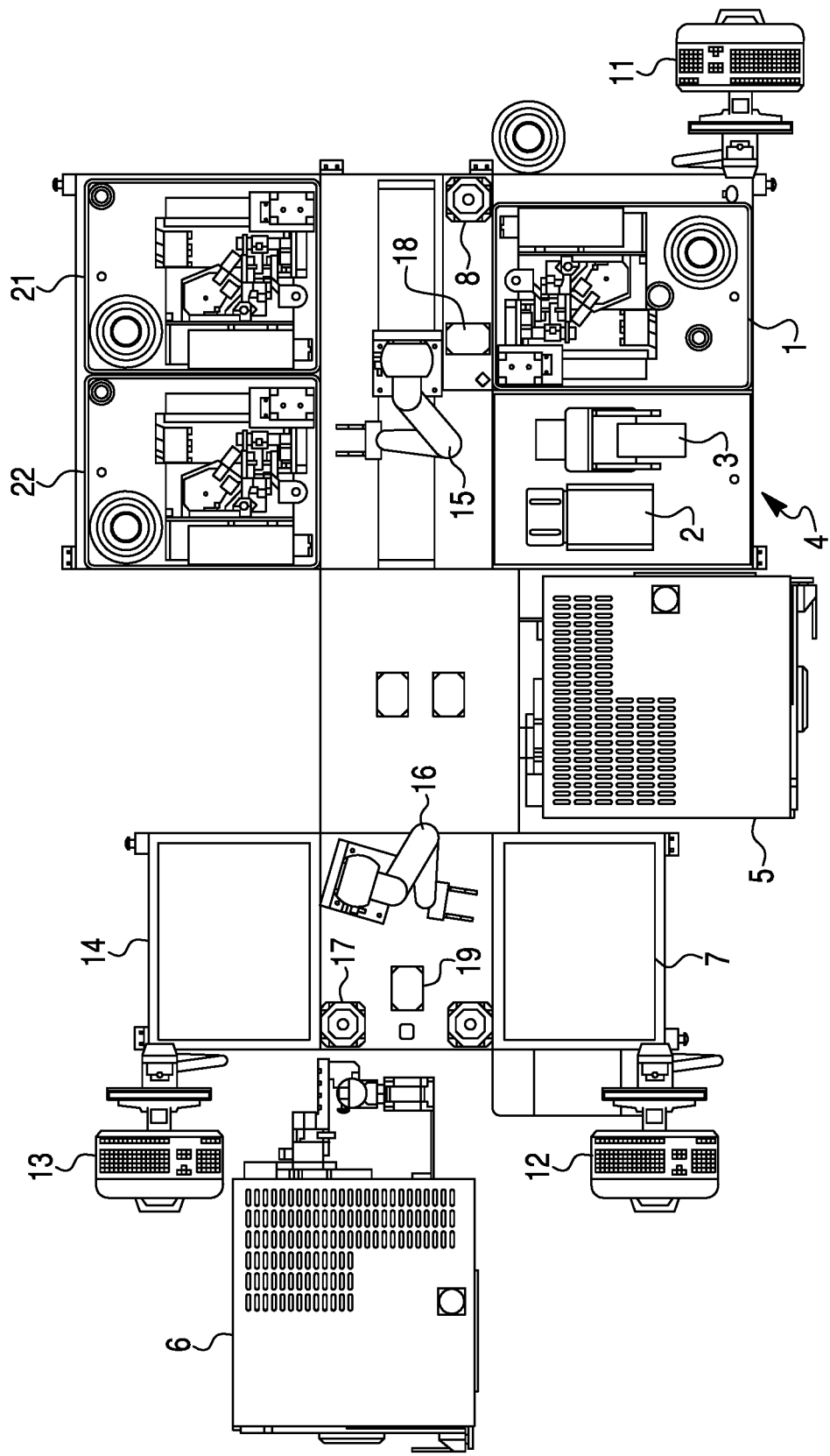
FIG. 15 shows a second non-limiting example of an automated insect bioassay system from a top view. The example illustrates a first sorting system, a piercing assembly, a sealing assembly, an evaporator, a first incubator, a second incubator, a first imaging assembly, a first plate storage assembly, a master computer, a second general computer, a third general computer, a second imaging assembly, a first robotic arm, a second robotic arm, a second plate storage assembly, a first barcode reader, a second barcode reader, a second sorting system, and a third sorting system.
Figure 16:
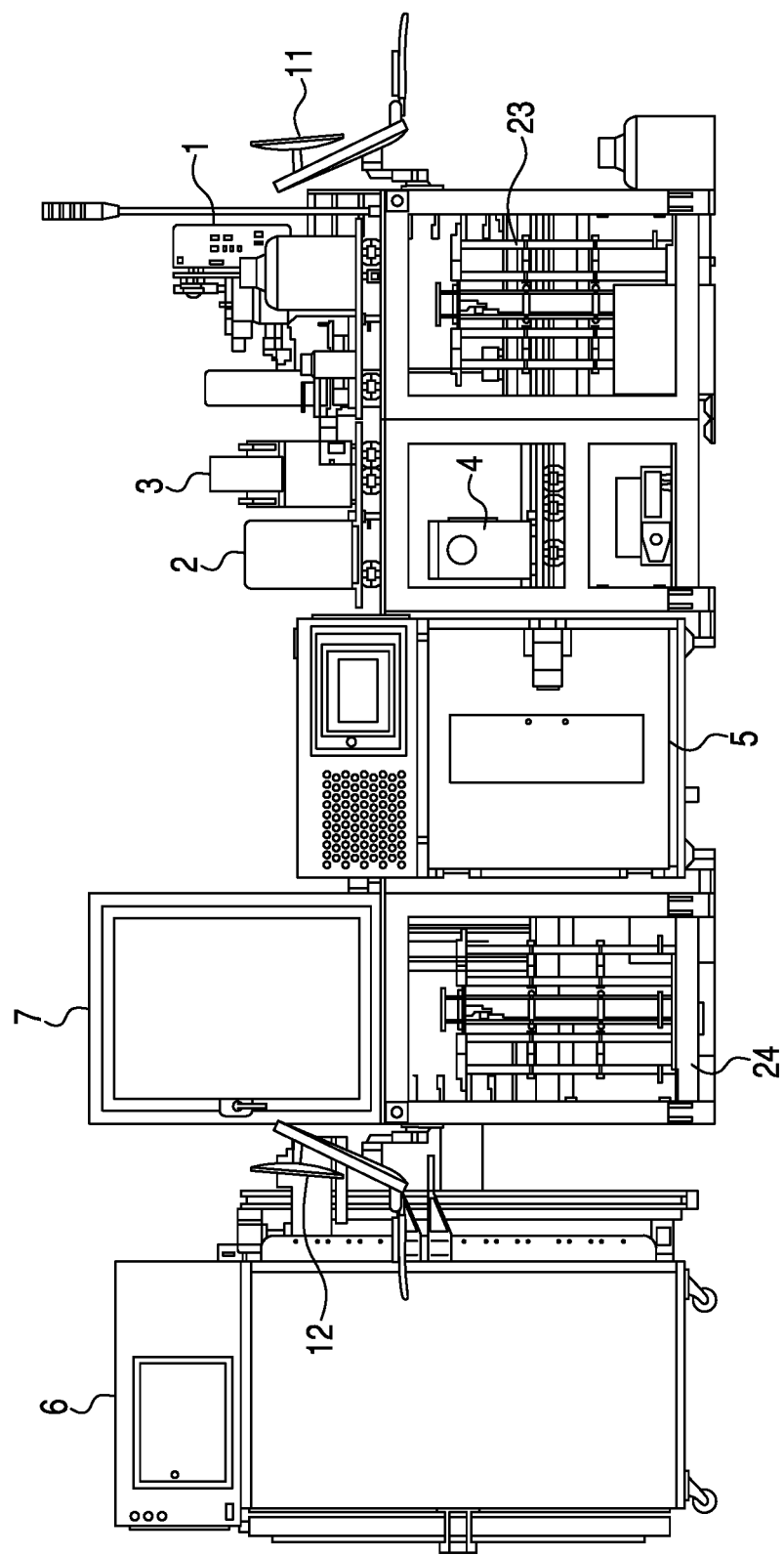
FIG. 16 shows the second non-limiting example of an automated insect bioassay system from a side view. The example illustrates a sorting system, a piercing assembly, a sealing assembly, an evaporator, a first incubator, a second incubator, a first imaging assembly, a master computer, a second general computer, and first and second plate stacking assemblies.

The control computer 101 can operate in a networked environment using logical connections to one or more remote computing devices 114a,b,c. By way of example, a remote computing device can be a personal computer, portable computer, smartphone, a server, a router, a network computer, a peer device or other common network node, and so on. Logical connections between the control computer 101 and a remote computing device 114a,b,c can be made via a network 115, such as a local area network (LAN) and/or a general wide area network (WAN). Such network connections can be through a network adapter, which can be implemented in both wired and wireless environments. Optionally, as depicted in FIGS. 15-16, the control computer 101 can function as a master computer 11, which can provide the processing circuitry for the robotic arm and be communicatively coupled to a robotic arm and other system components as further disclosed herein. The first and second imaging computers 12, 13 can also be connected to remote computing devices through the network 115. FIGS. 15-16 show a non-limiting example of such a configuration, in which the automated insect bioassay system includes a master computer 11 and first and second imaging computers 12, 13. The example illustrates a sorting system 1, a piercing assembly 2, a sealing assembly 3, an evaporator 4, a first incubator 5, a second incubator 6, a first imaging assembly 7, a first plate storage assembly 8, a master computer 11, a first imaging computer 12 (communicatively coupled to the first imaging assembly 7), a second imaging computer 13, a second imaging assembly 14 (communicatively coupled to the second imaging computer), a first robotic arm 15, a second robotic arm 16, a second plate storage assembly 17, a first barcode reader 18, a second barcode reader 19, a second sorting system 21, a third sorting system 22, a first stacking assembly 23, and a second stacking assembly 24.

In one exemplary configuration, the communication network 150 can be a LAN network that handles all scheduling instructions from control computer 101 to the imaging computers 12, 13 (for reading) and the sorting computers 120, 122, 124 (for sorting). In operation, the imaging computers 12, 13 can be dedicated to image acquisition and transfer of large amounts of image data to the network 115, and the remote computing devices 114a, 114b, 114c can download the image data and perform a series of image processing and statistics analysis. The communication network 150 can be self-contained, able to operate independently from the data network 140. Optionally, it is contemplated that each computer disclosed herein can comprise its own processing device (processor), a system memory, which includes a main memory (e.g., read-only memory (ROM), flash memory, dynamic random access memory (DRAM) such as synchronous DRAM (SDRAM) or Rambus DRAM (RDRAM), etc.) and a static memory (e.g., flash memory, static random access memory (SRAM), etc.), and a data (mass) storage device, which communicate with each other via a bus. The system memory typically contains data such as control processing data and/or program modules such as an operating system and control processing software that are immediately accessible to and/or are presently operated on by the processing unit. Optionally, any number of program modules can be stored on the mass storage device, including by way of example, an operating system and control processing software. Each of the operating system and control processing software (or some combination thereof) can comprise elements of the programming and the control processing software. Control processing data can also be stored on the mass storage device. Control processing data can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In alternative embodiments, a processor of a computer as disclosed herein represents one or more general-purpose processing devices such as a microprocessor, central processing unit, or the like. More particularly, the processor may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor may also be one or more special-purpose processing devices such as an application specific integrated circuit (ASIC), a field programmable gate array (FPGA), a digital signal processor (DSP), network processor, or the like. In alternative embodiments the processor is configured to execute the instructions (e.g., processing logic) for performing the operations and steps discussed herein.

In alternative embodiments the computer further comprises a network interface device (adapter). The computer also may include a display device, which can be a video display unit (display device, e.g., a liquid crystal display (LCD) or a cathode ray tube (CRT)). The computer also may include a human-machine interface, which can include, for example, an alphanumeric input device (e.g., a keyboard), a cursor control device (e.g., a mouse), and a signal generation device (e.g., a speaker). In addition to the human-machine interface, the computer may also include an input/output interface.

In alternative embodiments, the data storage device (e.g., drive unit) comprises a computer-readable storage medium on which is stored one or more sets of instructions (e.g., software) embodying any one or more of the protocols, methodologies or functions of this invention. The instructions may also reside, completely or at least partially, within the main memory and/or within the processor during execution thereof by the computer, the main memory and the processor also constituting machine-accessible storage media. The instructions may further be transmitted or received over a network via the network interface device.

In alternative embodiments the computer-readable storage medium is used to store data structure sets that define user identifying states and user preferences that define user profiles. Data structure sets and user profiles may also be stored in other sections of computer system, such as static memory.

In alternative embodiments, while the computer-readable storage medium in an exemplary embodiment is a single medium, the term "machine-accessible storage medium" can be taken to include a single medium or multiple media (e.g., a centralized or distributed database, and/or associated caches and servers) that store the one or more sets of instructions. In alternative embodiments the term "machine-accessible storage medium" can also be taken to include any medium that is capable of storing, encoding or carrying a set of instructions for execution by the machine and that cause the machine to perform any one or more of the methodologies of the present invention. In alternative embodiments the term "machine-accessible storage medium" shall accordingly be taken to include, but not be limited to, solid-state memories, and optical and magnetic media.

In alternative embodiments, information and signals are represented using any technology and/or technique known in the art. For example, data, instructions, commands, information, signals, bits, symbols, and chips used to practice the compositions (devices, computers) and methods of the invention can be represented by voltages, currents, electromagnetic waves, magnetic fields or particles, optical fields or particles, or any combination thereof.

In alternative embodiments, the various illustrative logical blocks, modules, circuits, and algorithm steps used to describe exemplary embodiments of the invention can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The algorithms and displays presented herein are not inherently related to any particular computer or other apparatus. Various general-purpose systems may be used with programs in accordance with the teachings herein, or it may prove convenient to construct a more specialized apparatus to perform the method steps. In addition, the present disclosure is not described with reference to any particular programming language. In alternative embodiments, a variety of programming languages are used to implement the embodiments of the invention as described herein.

Although the foregoing embodiments of the invention have been described in some detail by way of illustration and example for clarity of understanding, certain changes and modifications are encompassed within the scope of the appended claims.

The methods will be further understood by reference to the following non-limiting Examples. The following Examples are provided for illustrative purposes only. The Examples are included solely to aid in a more complete understanding of the described embodiments of the invention. The Examples do not limit the scope of the embodiments of the invention described or claimed.

Example 1: Preparation Procedure for WCRW Eggs

Figure 2A:
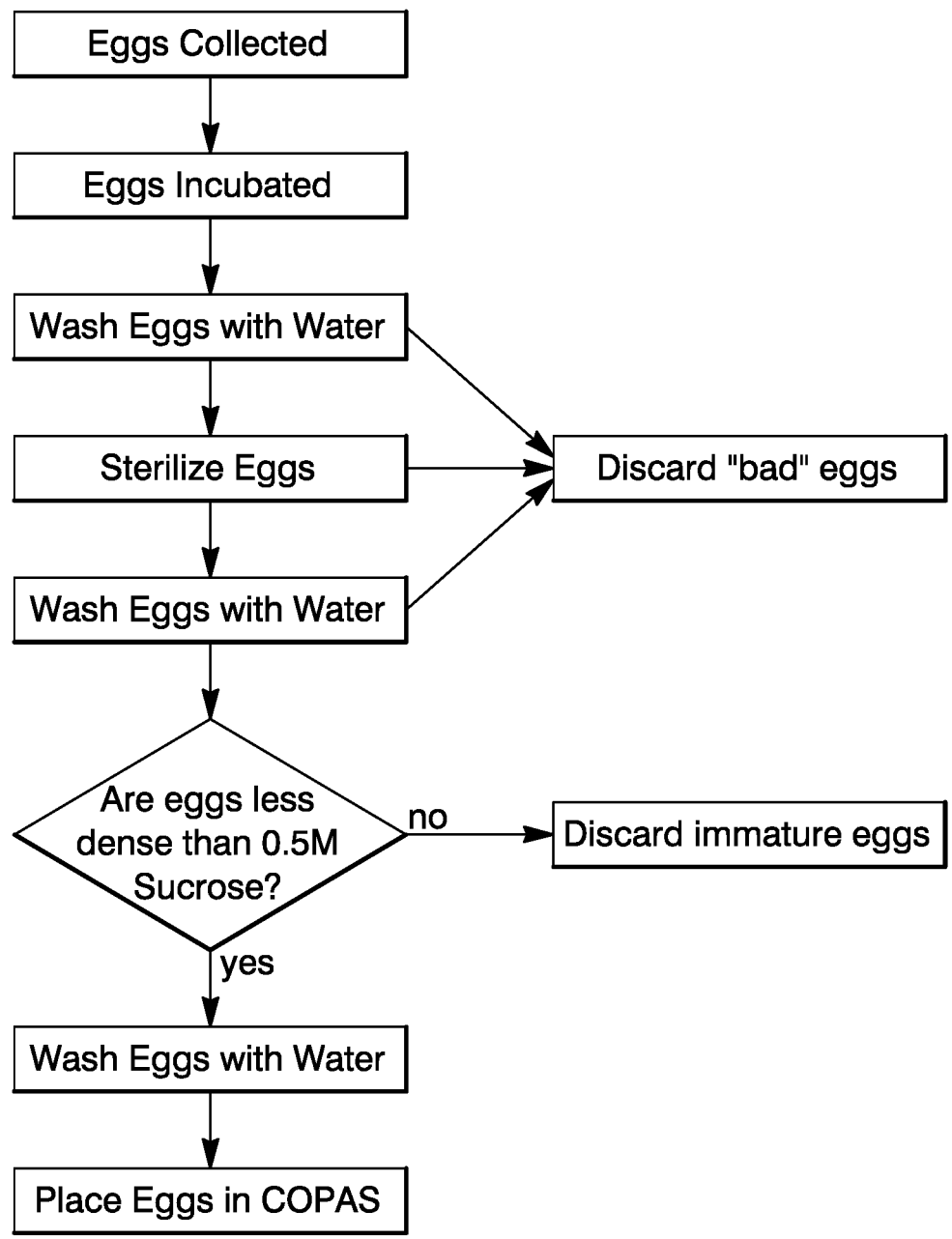
FIG. 2A: Exemplified insect egg preparation *Diabrotica virgifera* (WCRW).

The *Diabrotica virgifera* (WCRW) eggs were kept for 10 days at 28° C. before sterilization and preparation for processing using a COPAS sorting system. The eggs, which were contained in layers of cheesecloth, were placed in petri dishes filled with a solidified agar solution. When the eggs were ready (as determined by changes in egg appearance), they were rinsed off the cheese cloth into a 600 μm standard metal sieve on top of a 180 μm sieve. Once all the eggs were collected, the eggs were then placed into a container, and rinsed several times with water to remove bits of cheese cloth and other dirt from the colony. The floating eggs and larvae were broken shells and unusable eggs, and the sinking eggs were whole and mature eggs. Floating eggs and larvae were removed. The remaining eggs were sterilized using bleach, Peracetic Acid and Ethanol. After each solution the eggs were rinsed several times with deionized water to remove any chemicals. After sterilization, eggs were placed in a graduated cylinder containing 0.5M sucrose solution to separate immature eggs from mature. The eggs were allowed to equilibrate for 30 min, at which time the floating eggs were considered viable eggs. The final eggs were washed with water several times before adding to the COPAS® sorting system (FIG. 2A). Eggs determined to be as "non-viable" (floating in original water rinse, and sinking in sucrose solution, see Table 1) were not used.

TABLE 1

Egg hatch rate and infestation time for WCRW when exposed to a sucrose gradient

| Egg Population Density | Hatch % | Time (min) per plate |
|---|---|---|
| whole population | 90-84 | 7-12 |
| Heavier than 0.5 M Sucrose | 36-33 | 3-9 |
| Lighter than 0.5 M Sucrose | 91-82 | 1-3 |
| Lighter than 0.37 M Sucrose | 91-89 | 3-4 |

Example 2: Preparation of Loose Lepidoptera Eggs

Figure 2B:
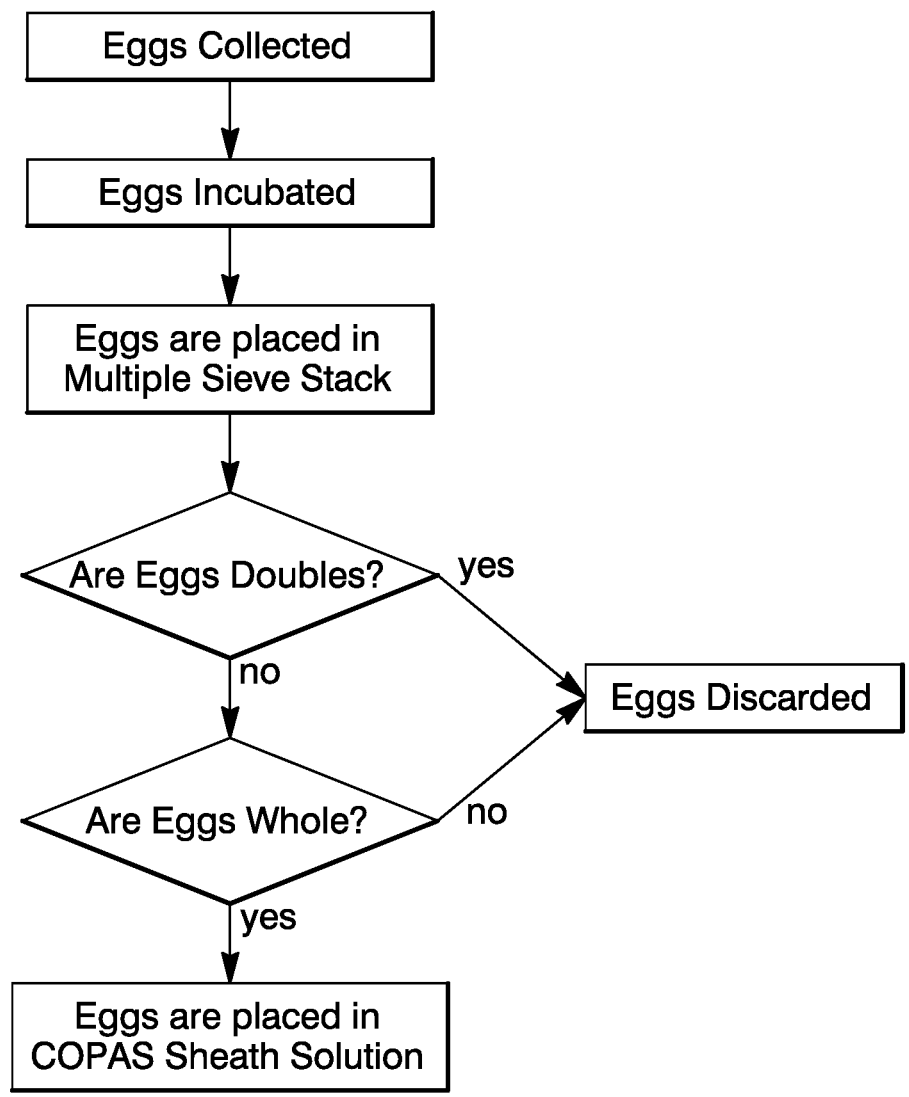
FIG. 2B: Exemplified insect egg preparation *Anticarsia gemmatalis* (VBC), *Helicoverpa zea* (CEW) and *Spodoptera frugiperda* (FAW).

The Lepidoptera (*Anticarsia gemmatalis* (VBC), *Heliothis zea* (CEW) and *Spodoptera frugiperda* (FAW)) eggs were placed in a stack of sieves. The top sieve was sized 710 μm or 600 μm and removed egg clumps from the mix. The bottom sieve was 425 μm, and eggs that passed through were small, desiccated, and/or broken. The eggs were incubated at 22-32° C. for 20-26 hours. When the eggs showed signs of development (darkened color, and internal movement), the mature eggs were removed, sieved a second time, and placed in a solution of COPAS® Sheath Concentrate and deionized water (1 mL/L). The eggs were immediately loaded into the sample container of the COPAS® system for infesting (FIG. 2B).

Figure 2C:
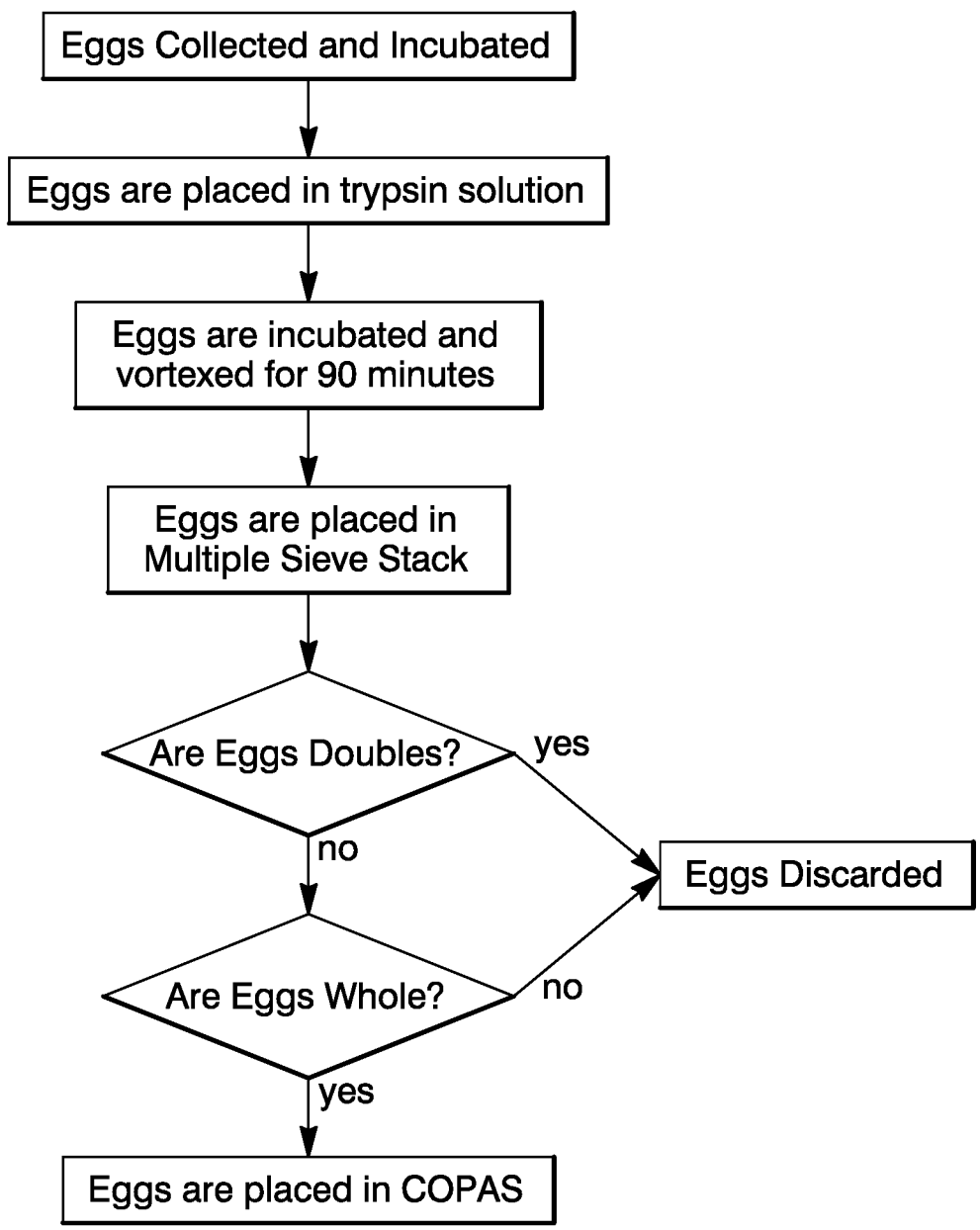
FIG. 2C: Exemplified insect egg preparation *Ostrina nubilais* (ECB).

Example 3: Preparation of ECB Eggs or ECB Larval and Selective Larval Dispensing by a Sorting System The *Ostrina nubilais* (ECB) egg masses were incubated until they showed signs of development. Approximately one gram of egg masses was placed into a 50 mL conical tube containing 10 mL of freshly prepared 5 mg/mL trypsin solution (50 mM TRIS HCL, pH8) to digest the proteins holding the individual eggs in a mass. The digestion separated the ECB eggs so they could be run individually through the COPAS® large particle sorter. The conical tube containing the ECB egg-trypsin solution was incubated at 33° C. for a total of 60 minutes. Every 15 minutes the tube was removed and agitated for 30 seconds then returned to the incubator for the next 15 minute incubation period. The process was repeated 4 times. After 60 minutes the majority of eggs were separated. To rinse residual digest reagents from the eggs a solution of 1 mL COPAS® sheath concentrate/L of deionized $H_2O$ (heretofore referred to as "sheath solution") was added to the conical tube and agitated for several seconds. The eggs were allowed to settle and the liquid decanted until the bulk of material left in the tube were eggs. The sheath solution wash was repeated three times. The eggs were passed through a 600 μm sieve using a sheath solution rinse to separate undigested masses and emerged larvae from single eggs. The eggs were immediately loaded into the sample container of the COPAS® system for infesting (FIG. 2C).

*Ostrina nubilais* (ECB) neonate larvae in a hatch container were transferred to a $CO_2$ chamber, where the larvae were exposed to $CO_2$ gas for 15-25 seconds. The hatch container was removed from the chamber and treated larvae were transferred from the hatch container to a 710 μm sieve by gently spraying the contents with a solution of 5 mL COPAS® sheath concentrate/L of deionized $H_2O$ (heretofore referred to as "sheath solution"). Larvae were collected, along with the sheath solution, in a holding container before being loaded into the sample container of the COPAS® system for infesting.

The COPAS® FP 1000 sorting system (Union Biometrica, Holliston, MA) was used to deliver individual eggs to each well of an assay plate. The COPAS® FP sorting system used pressure to feed larvae through a flow cell with optical detectors that simultaneously detected green and red fluorescence, optical density (or optical extinction, EXT) and axial length (or Time of Flight, TOF) excited by a 488 nm solid state laser. The following acquisition parameters have been optimized for insect larvae sorting: Green PMT (Photo multiplier tube) at 450, Side Scatter PMT at 100, Red PMT at 500, and pure coincidence mode (no super drops or multiple event allowed). The delay and width parameters may vary depending on the size and shape of the larvae (delay range 10-16 ms; width 5-10). Detection thresholds were set to 50 (signal) and 600 (time of flight). The EXT along with TOF was used to identify objects that were individual larva (i.e., removing conjoined larvae), and those larvae most likely to be intact after preparation for COPAS® sorting. Larvae with low EXT and high TOF may be more likely to be single, viable organisms. Unselected larvae were moved to the waste container. Sheath pressure (deionized water was used instead of Sheath medium) was kept at a value of around 1.80 psi, sorter pressure 1.03 psi, while sample pressure was kept to 0.4-0.50 psi. The flow rate was kept below 10 detected objects per second by adjusting mixing speed (ranging from 35-45%). Each larva was delivered to a well with a small amount of sheath fluid (less than 10 μL). Once the plate was infested with one larva per well, the control computer of the system signaled the robotic arm to move the assay plate to the Ultravap® evaporator, which dried the remaining sheath fluid, to prevent the larvae from drowning. The plate was then sealed by an automatic plate sealer, and air holes in communication with each well were punched with a modified plate piercer. The plate piercing assembly was modified from its factory design to have smaller pins (with a diameter of less than 0.5 mm) and to have a configuration of pins in which at least two pins penetrated each well.

Example 4: Automated Plate Preparation and Infestation Process

The infesting system included both plate processing tasks and infesting.

Figure 3:
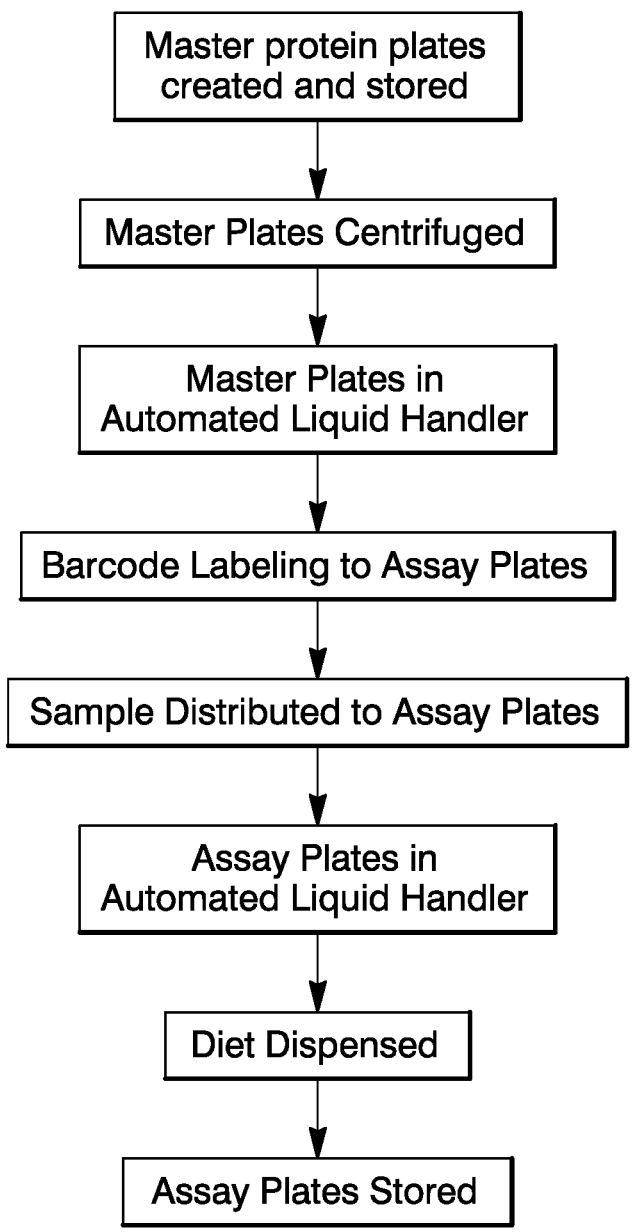
FIG. 3: Exemplified assay plate preparation.
Figure 4:
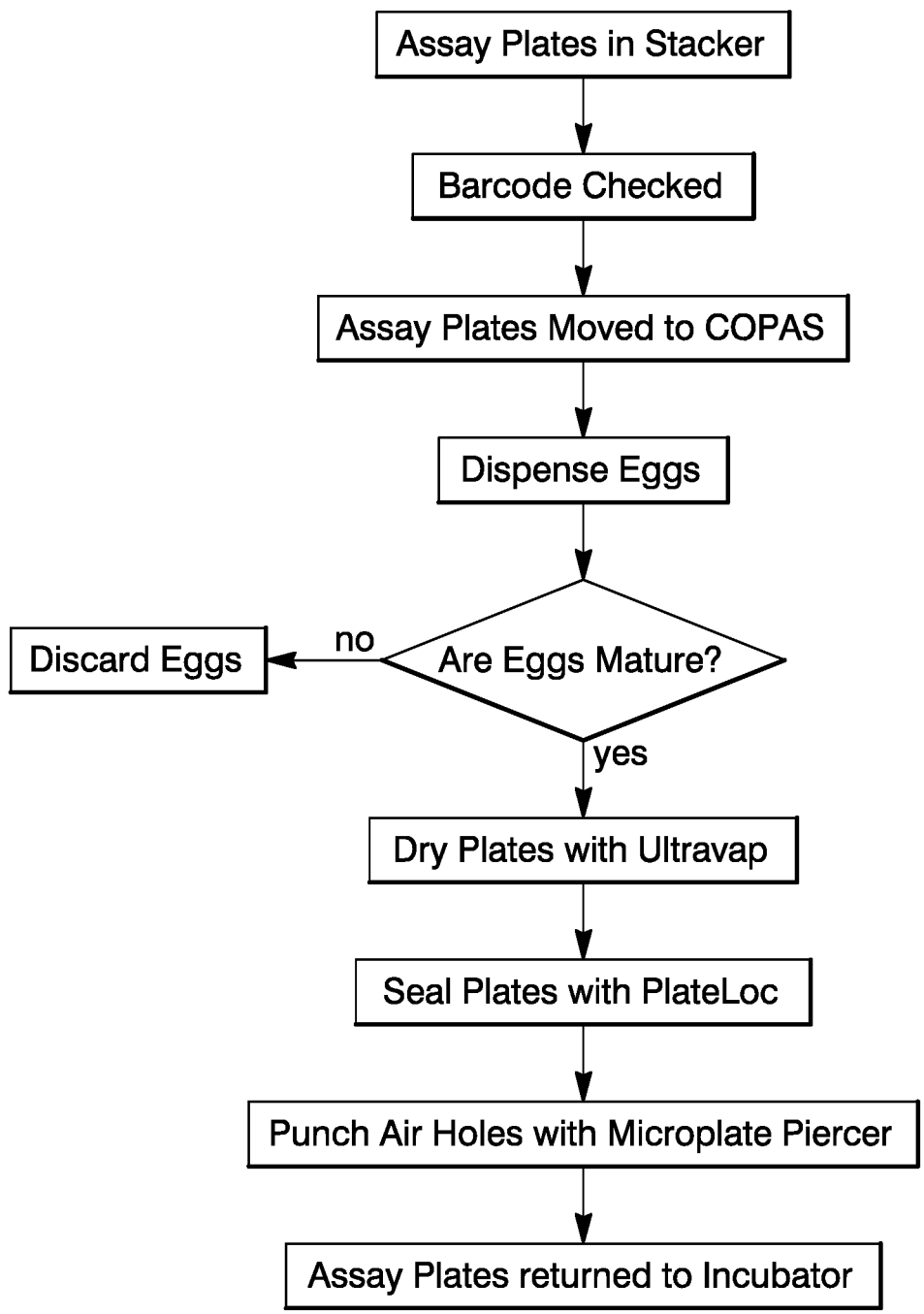
FIG. 4: Exemplified infestation and plate processing.

Sample preparation (FIG. 3): Each protein sample was plated in a 96 well round bottom plate, each of which can carry between of 3 to 24 assay plate replicates. The prepared plates of protein for testing were stored at 4° C. to minimize protein degradation. The assay plate creation used an automated liquid handler connected to an automated barcode labeler. The automated barcode labeler adhered a unique, standardized barcode to each plate. The automated liquid handler dispensed 10-30 μL of sample into each well. The plates were transferred to a second automated liquid handler to dispense insect diet (Southland Products, Lake Village, AR for Lepidoptera or Frontier Agricultural Sciences, Newark, DE for Coleoptera, or a non-standard diet containing various amounts of antibiotics or antifungal agents made either by Southland or Frontier). For the Coleoptera assays, each of the dry ingredients was processed with a coffee grinder to decrease particle size and minimize background noise for the imaging process. Additionally, 15 mL black food coloring was also added, which decreases the natural fluorescence in the diet and increases the contrast between the diet and the larvae. Neither grinding or food coloring is needed for the Lepidoptera assays. The diet was dispensed into each well of the assay plate using a modified automated liquid handler with a heated reservoir with a magnetic stirring mechanism to continuously mix the ingredients. Each well received 25-60 µL diet, which was shaken immediately at 1500 rpm for 75 seconds.

Infestation by a Sorting System (FIG. 1): The plates were first introduced to the system from an Agilent® Labware Stacker (Agilent® Technologies, Santa Clara, CA). A Direct Drive Robotic Arm (Agilent® Technologies, Santa Clara, CA) moved each assay plate to the barcode reader, and then the COPAS® sorting system. After infesting with the COPAS®, the robotic arm moved the plate on to the Ultravap® RC Microplate evaporator, which used heated dry air to evaporate fluid dispensed by the COPAS®. The Ultravap® evaporator dried CEW, ECB (eggs), and FAW plates for 90 seconds using 29° C. air at 11 PSI. The WCRW plates with two eggs per well were dried for 120 seconds using 29° C. air at 11 PSI. The ECB (larvae) plates were dried for 60 seconds using 29° C. air at 11 PSI. The plates were then moved by the robotic arm to the plate sealer (Agilent® PlateLoc), which sealed each plate using a clear, heat activated adhesive seal. The plates were allowed to rest for 30 seconds to return to room temperature, when a robotic arm moved the plate to the Agilent® Microplate Piercer to create small air holes in the clear seal. The assay plate was then placed in the incubator by the robotic arm, either at 25° C. or 28° C. for 20 hours before starting imaging.

Example 5: Selective Egg Dispensing by a Sorting System

The COPAS® FP 1000 sorting system (Union Biometrica, Holliston, MA) was used to deliver individual eggs to each well of an assay plate. The WCRW were infested on black ProxiPlates. The CEW, ECB, VBC, and FAW were infested on white ProxiPlates. The COPAS® FP sorting system used pressure to feed eggs through a flow cell with optical detectors that simultaneously detected green and red fluorescence, optical density (or optical extinction, EXT) and axial length (or Time of Flight, TOF) excited by a 488 nm solid state laser. For sorting insect eggs, a 488 nm 10× clean up filter was used for quenching the excessive intensity from side-scattering, the reflection of laser off the surface of eggs. The following acquisition parameters have been optimized for insect egg sorting: Green PMT (Photo multiplier tube) at 450, Side Scatter PMT at 100, Red PMT at 500, and pure coincidence mode (no super drops or multiple event allowed). The delay and width parameters may vary depending on the size and shape of the egg (delay range 10-16 ms; width 5-9 ms). Detection thresholds were set to 50 (signal) and 600 (time of flight). The EXT along with TOF was used to identify objects that were individual eggs (i.e., removing eggs that are stuck together). The red fluorescence was detected through a 615/24 filter (Center Wavelength 615 nm, and Guaranteed Minimum Bandwidth 24 nm). The green fluorescence was detected through a 510/23 filter (Center Wavelength 510 nm, and Guaranteed Minimum Bandwidth 23 nm). The side scatter was detected through the 488 nm emission filter. Sheath pressure (deionized water was used instead of Sheath medium) was kept at a value of around 1.80 psi, sorter pressure 1.03 psi, while sample pressure was kept to 0.4-0.50 psi. The flow rate was kept below 20 detected objects per second by adjusting mixing speed (ranging from 45-85%). Each egg has a distinct extinction, time of flight, amount of green, amount of red, and amount of side scatter. Eggs that are more likely to hatch may have lower extinction and side scatter values compared to eggs that were not ready to hatch (Table 2). Using light thresholds that included detected extinction, detected green light, detected red light, detected side-scatter and detected object time of flight (settings that differ for each species), the COPAS® selected eggs that were more likely to hatch, and moved eggs unlikely to hatch to the waste container. Each egg was delivered to a well with a small amount of sheath fluid (less than 10 µL). Once the plate was infested with one egg per well, the COPAS® signaled the robotic arm to move the assay plate to the Ultravap® evaporator, which dried the remaining sheath fluid, to prevent the eggs from drowning. The plate was then sealed by an automatic plate sealer, and air holes were punched with a modified plate piercer. The robotic arm sequentially transported the plate from the evaporator to the plate sealer and from the plate sealer to the plate piercer.

TABLE 2

Effect of the ratio between extinction and side scatter on hatch rate and infestation time for WCRW.

| Parameters | Hatch Rate % | Time (min) per plate |
| --- | --- | --- |
| Ratio > 108 | 64-79 | 1.5-2 |
| Ratio > 124 | 87-94 | 3-4.5 |

Ratio = 100 × Peak Height Extinction/Peak Height Side Scatter.

Example 6: Imaging Cycles and Image Pre-Processing

Figure 5:
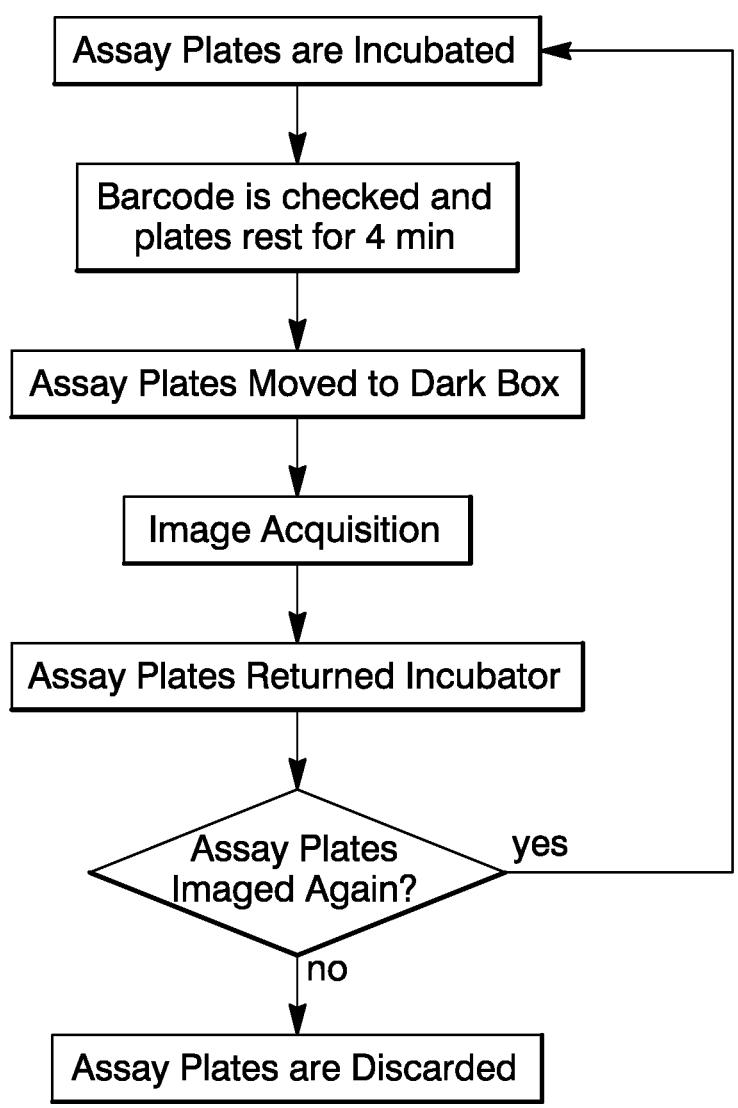
FIG. 5: Exemplified incubating and imaging cycles. Images may be taken on day 1 and day 3, or on day 1, 4, or day 1 and 6 (twice) depending on plate variations.

Each assay plate was incubated at either 25° C. or 28° C. for 20 hours after infestation (FIG. 5). The plates were removed from the automated incubator (by the automatic incubator), then the Direct Drive Robotic Arm moved each assay plate to the barcode reader, followed by a MiniHub (Agilent® Technologies, Santa Clara, CA), where the plates rested for 4-10 minutes to bring them to room temperature and minimize condensation. Each plate was then moved to a Nikon® AZ100 microscope by the robotic arm. The plate was illuminated with a Lambda LS xenon arc lamp or a Lambda HPX High Output LED. The light was filtered using a FITC filter (480 nm ex, 540 nm em). One image was taken of either each well individually, or a group of 4 wells, in a 96 well plate; each image was taken with 200-400 ms exposure and saved as 14-bit tiff format with a resolution of 1392×1040 pixels. The robotic arm then placed the plates back in the incubator (either at 25° C. or at 28° C.) for 6 to 48 hours before the next imaging cycle.

Figure 6:
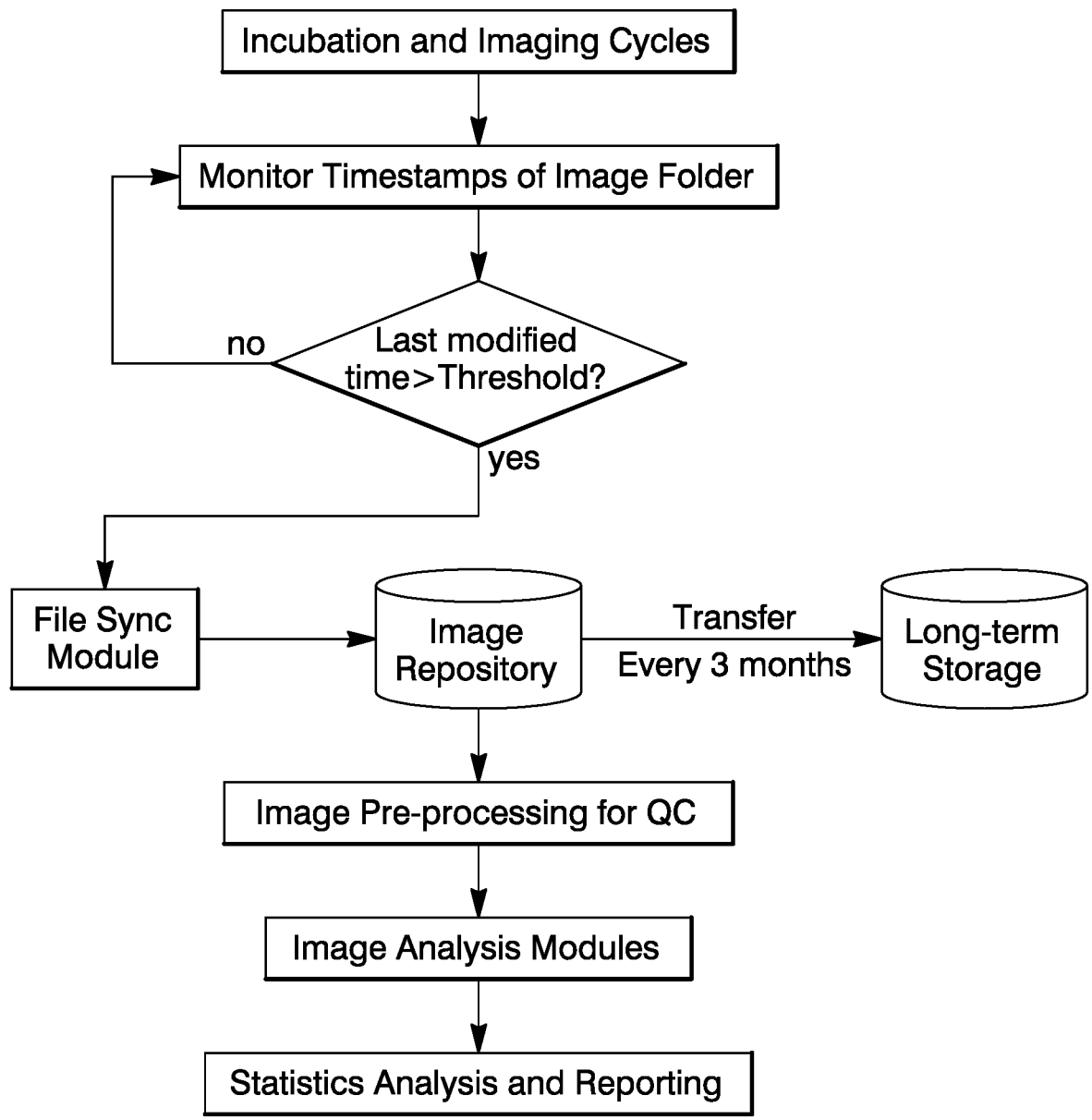
FIG. 6: Exemplified image auto-copy, pre-processing and image-analysis are carried out through recurring scheduled jobs.

During each imaging cycle, images of selected subsets of plates were temporarily stored in a file system containing sub-directories. Sub-directories are labeled "Day1", "Day2", . . . "DayN", in which "1, 2, . . . , N" represent the number of days elapsed after the day that an infestation run was completed for any given plate set. An automated copy program "autocopy.pl" was implemented in Perl script and driven by ActivePerl v5.18. The main utility of the autocopy program was to transfer large numbers of image files that reside in the above mentioned sub-directories, organize them by date of infestation, batches/subsets of plates and then by elapsed day of imaging, to a centralized server that mainly serves as an image repository. The autocopy program copies thousands of image files within 10-30 minutes, interlacing with imaging acquisition runs. On the image repository server, all folders containing images were shared on a network drive for image-processing servers and regularly transferred to long-term image storage about every 3 months (FIG. 6).

Pre-processing was conducted by a program named "imagestitch.pl". It utilized a combination of Perl script and imagemagick 6.8.2 functions to create a montage image consisting of 96 wells in 8 row×12 column format, for each plate at any given elapsed days. The resulting montage image served as a way for researchers to visually quality-assure the images based on layout of submitted samples in 96-well plates. The links to stitched montage images were reported together with the final statistical analysis report (FIG. 6).

Example 7: Image Analysis Process

Figure 7:
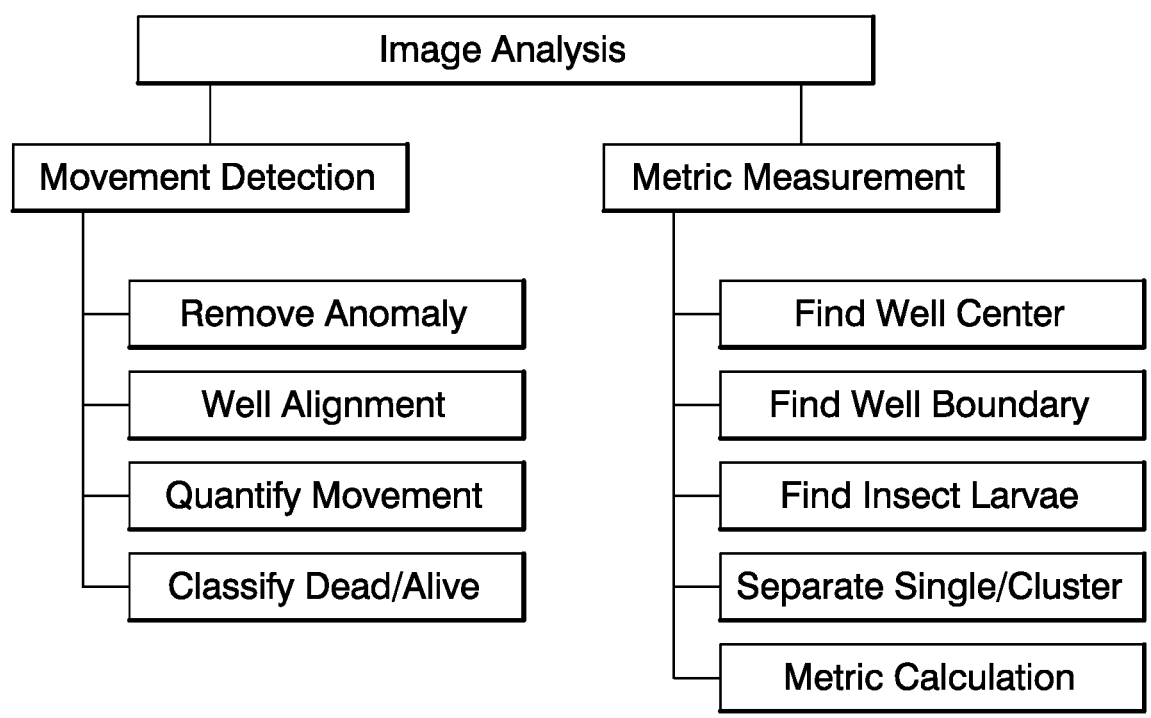
FIG. 7: Steps for two methods of image analysis module.
Figure 8:
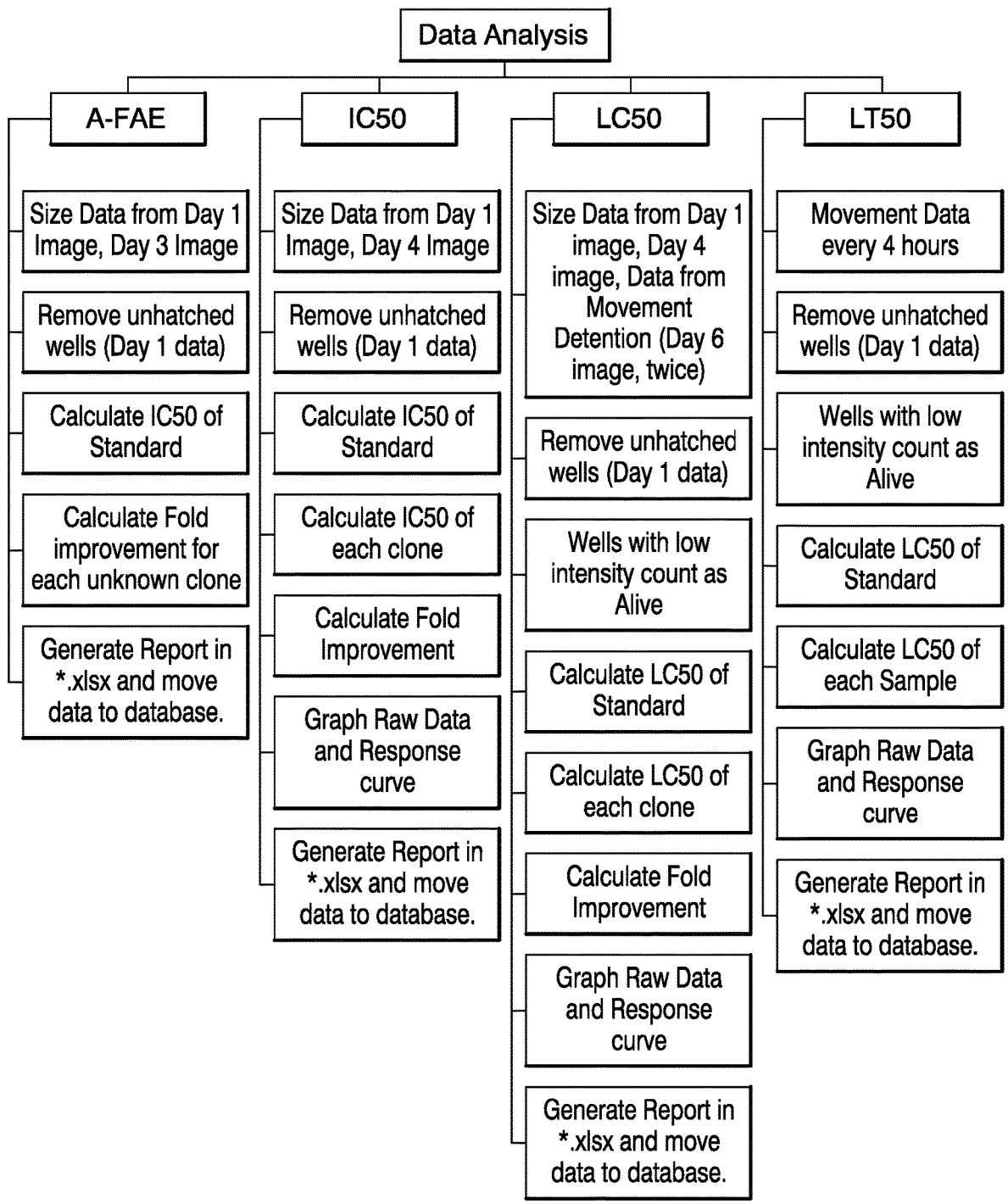
FIG. 8: Exemplified statistics analysis and reporting.
Figure 9A:
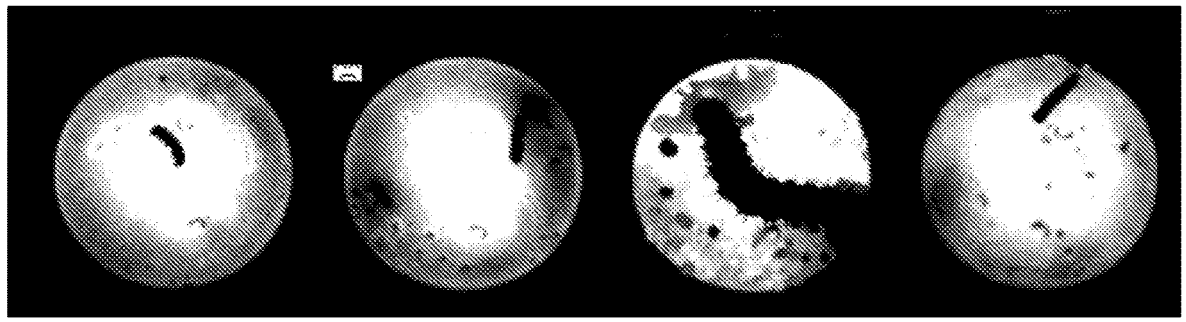
FIG. 9A is an image of four wells from one assay plate taken on day 6.
Figure 9B:
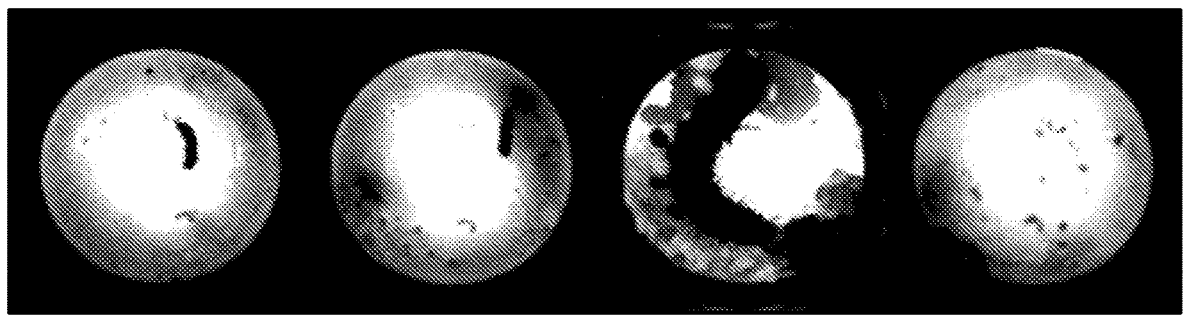
FIG. 9B is a second image of the four wells of FIG. 9A taken four hours later.
Figure 9C:
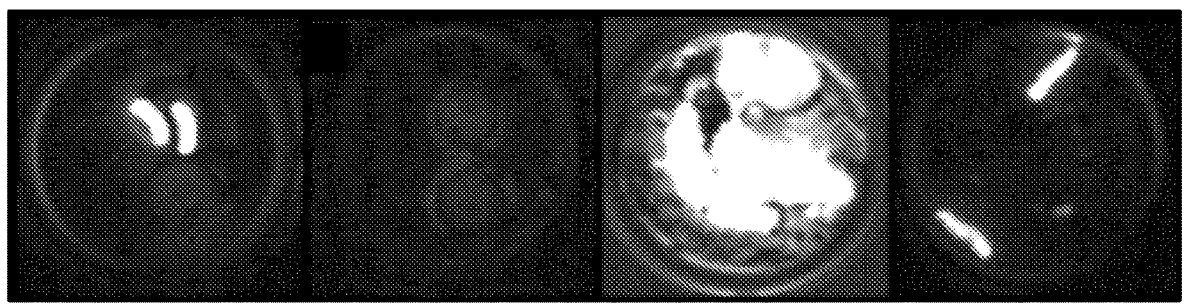
FIG. 9C is an overlay of FIGS. 9A and 9B. In the overlay, regions of difference between two images (larva movement) are denoted by white.
Figure 13:
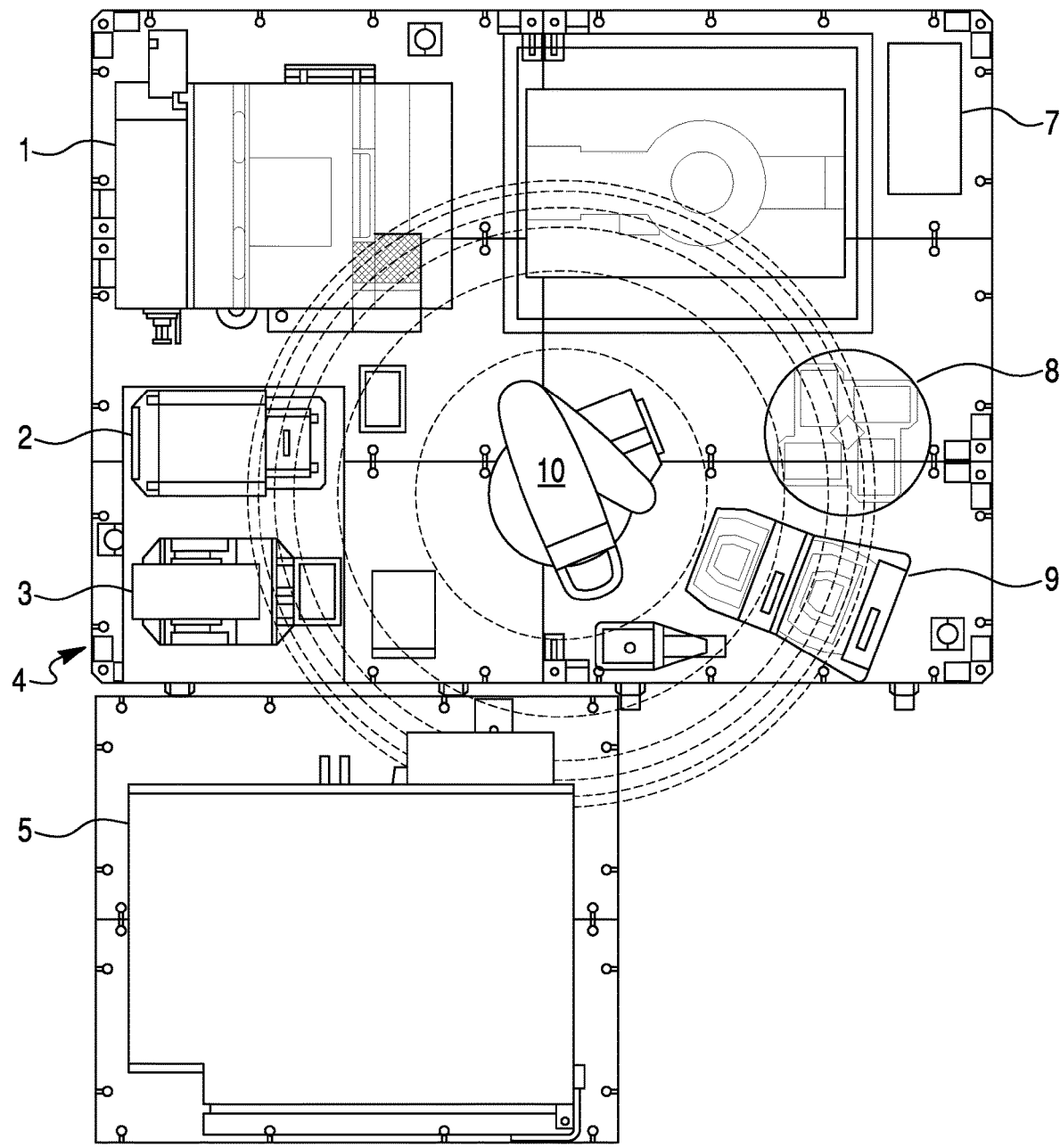
FIG. 13 shows a first non-limiting example of an automated insect bioassay system from a top view. The example illustrates a sorting system, a piercing assembly, a sealing assembly, an evaporator, a first incubator, an imaging assembly, a plate storage assembly, a plate stacking assembly, and a robotic arm.
Figure 14:
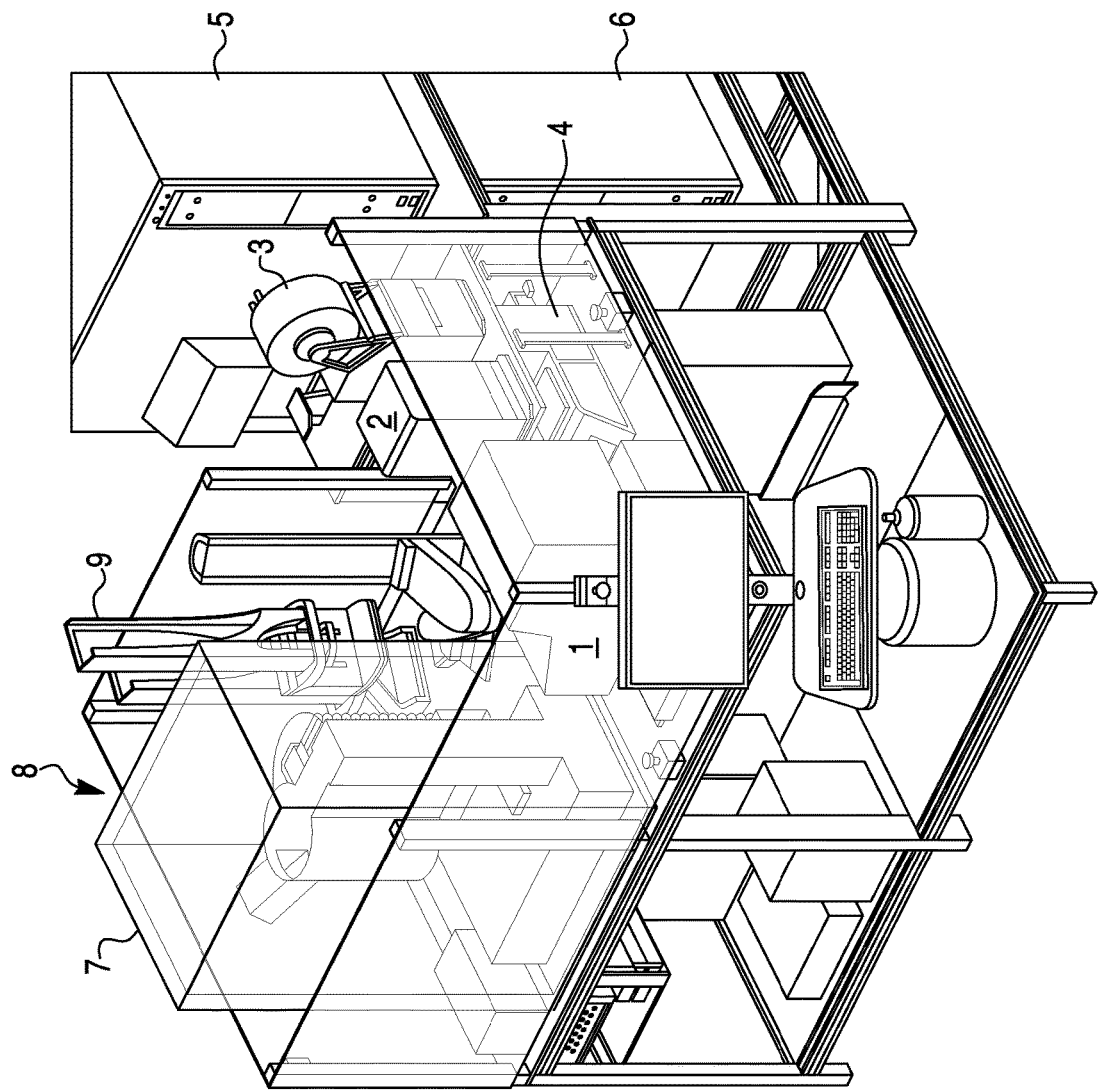
FIG. 14 shows the first non-limiting example of an automated insect bioassay system from a side view. The example illustrates a sorting system, a piercing assembly, a sealing assembly, an evaporator, a first incubator, a second incubator, an imaging assembly, a plate storage assembly, and a plate stacking assembly.

Image analysis included two major methods: movement detection and metric measurement (FIG. 7). Based on the empirical observation of hundreds of assay plates, insect movement was discovered and determined to be of high correlation (>0.95) with insect survival. Movement detection was therefore a good surrogate step to determine the mortality of the test organism, based on two consecutive time-lapse images of the same well on the same assay plate that were acquired at 4-hour interval (see FIGS. 9A-9C). The movement detection program consisted of four steps and was written in Matlab (Matlab version R2014a): 1) an anomaly removal step detected any high light intensity or low light intensity stripes resulted from shutter control misfire and modify the original tiff image to remove the anomaly; 2) aligned two images to eliminate any random translational mis-alignment of two time-lapse images; 3) created a sum of the pixel-level difference of aligned portions of two images; and 4) classified well based on the sum of pixel difference to predict whether there are significant movements within the well between 4 hours' time interval. The result was a binary dead/alive prediction with confidence level that was used in a LC-50, EC-50 and LT-50 analysis (FIGS. 10A-10B).

Metric measurement was a further step of the image analysis. The metrics reported included pixel area of larvae, x-y-coordinate of larvae center larvae light intensity, well (contrasting background) area, well light intensity, larvae length, larvae thickness, well classified as empty (no larvae hatched), well classified as heavily consumed (low overall light intensity). The imaging analysis results were exported over the data network as a consolidated table and saved as comma delimited values (csv) format. The result was a measurement of individual organism size that can be used in IC-50 or EC-50 analysis (FIGS. 10A-10B).

Example 8: Statistical Analysis based on Size Measurements

Image analysis created the larvae location within the well, the pixel area of each larvae, the larvae light intensity, the well area intensity, and the length and thickness of each larvae. When a larva was not found in a well, a value returned was 0. Each well with 0 was to be converted to not available (NA). Any larvae that hatched more than 20 hours after infest was removed from the analysis.

The first tier system or Automated Fast Activity Evaluation (A-FAE) was tested using insects grown in assay plates for 3 days (after infest). Each assay plate consisted of 80 insecticidal proteins and an assay standard. The assay standard was a purified insecticidal protein known to be efficacious against the test organism. The standard was placed in two wells at a dose high enough to cause 100% mortality, and diluted by half for 8 total doses (two wells contain each concentration for a total of 16 wells of assay standard on each assay plate). The protein mother plate was replicated 12 times (12 replicates of each clone and 24 replicates of each dose of the assay standard). This group of assay plates was accompanied by 3 control plates containing buffer. The EC-50 or IC-50 for the assay standard may be calculated using the buffer plates as the zero dose, and the assay standard to calculate the dose response curve (a 4 parameter log-logistic curve). The curve fit was calculated in R using the package "drc" (Ritz & Streibig, 2005) Journal of Statistical Software 12: 1-22. The dose for each unknown clone was fitted into a standard dose response curve, and a predicted larva size was returned (FIGS. 10-12). When this size was divided by the observed larva size (median size out of 12 replicates), an index value was returned representing a potential fold improvement over the assay standard. Clones that had an index value greater than 1.0 are moved on to the second tier testing.

Example 9: Mortality Determination and LT-50 Analysis

The LT-50 (time at which 50% of the insect are dead) was calculated for each insecticidal protein. Mortality was determined by comparing two images using the imaging system (see example 7). The images were taken between 4-24 hours apart for mortality observations. Large larvae that had consumed a majority of diet in a well (resulting in decreased well intensity readings) and whose body occupied a majority of the volume of the well (resulting in restricted larval movement), were reported "dead" by the movement detection program. Larvae were reclassified as "alive" based on relative well intensity. The assay plate design was the same as Example 8. The frequency of mortality (number of "Dead" vs number of "Alive" larvae) was used in the General Linear Model (Probit fit) to determine the LT-50 of each clone and the assay standard (FIG. 12).

What is claimed is:

1. An automation system for assaying the activity of insecticidal compounds in a high throughput mode comprising:
   a. a sorting system capable of dispensing insect eggs into a multi-well plate, wherein the sorting system comprises:
      i. a flow channel configured to deliver insect eggs from the sorting system to the multi-well plate;
      ii. an illumination source configured to illuminate insect eggs within the flow channel; and
      iii. an optical detector, wherein the optical detector is configured to measure time of flight or optical density of a respective insect egg when the illumination source illuminates said insect egg within the flow channel; and
      iv. a processor, wherein the processor is communicatively coupled to the optical detector and configured to determine insect eggs that are likely to hatch based on the measured time of flight or optical density of the insect eggs that are delivered to the multi-well plate;

b. a robotic arm configured to transport the multi-well plate;

c. a measuring device, wherein the measuring device is capable of measuring movement or determining a metric measurement within a plate of the multi-well plate; and d. a control computer, wherein the control computer is communicatively coupled to the processor of the sorting system, the robotic arm, and the measuring device, and wherein the control computer is capable of coordinating the functions and timings of the sorting system, the robotic arm, and the measuring device of the automation system.

2. The system of claim 1, further comprising a data storage device.

3. The system of claim 2, wherein the data storage device comprises a server connected to the measuring device through a local area network.

4. The system of claim 3, wherein the measuring device comprises a camera configured to capture images of one or more wells of the multi-well plate, and wherein the data storage device is configured to store the images of the one or more wells in a file system.

5. The system of claim 1, wherein the sorting system is a large particle sorter.

6. The system of claim 5, wherein the sorting system is a large particle flow cytometer.

7. The system of claim 1, further comprising an automated plate labeler.

8. The system of claim 1, further comprising an automated liquid handling robot for dispensing artificial insect diet into the multi-well plate.

9. The system of claim 1, further comprising a drying device.

10. The system of claim 1, further comprising a sealing device.

11. The system of claim 1, further comprising an incubation device capable of controlling temperature and humidity.

12. The system of claim 11, wherein the incubation device is capable of automatically transporting, tracking, and retrieving multi-well plates.

13. The system of claim 1, wherein the measuring device comprises a sensor, a camera, or a microscope.

14. The system of claim 1, further comprising a scheduling software platform to control all or part of the measuring device, data storage device, and the control computer.

15. The system of claim 1, wherein the illumination source comprises at least one visible laser.

16. The system of claim 1, wherein the optical detector is configured to measure time of flight and optical density of the insect eggs.

17. The system of claim 1, wherein the optical detector is configured to measure fluorescence emissions of the insect eggs.

18. The system of claim 1, wherein the processor of the sorting system is configured to determine insect eggs that are likely to hatch, at least in part, by comparing the measured time of flight or optical density of respective insect eggs to predetermined thresholds for time of flight or optical density.

19. The system of claim 16, wherein the processor of the sorting system is configured to determine insect eggs that are likely to hatch, at least in part, by comparing the measured time of flight and optical density of respective insect eggs to predetermined thresholds for time of flight and optical density.

20. The system of claim 1, wherein the optical detector is configured to measure time of flight of a respective insect egg when the illumination source illuminates said insect egg within the flow channel, and wherein the processor of the sorting system is configured to determine insect eggs that are likely to hatch, at least in part, by comparing the measured time of flight of respective insect eggs to a predetermined threshold for time of flight.

21. The system of claim 1, wherein the optical detector is configured to measure optical density of a respective insect egg when the illumination source illuminates said insect egg within the flow channel, and wherein the processor of the sorting system is configured to determine insect eggs that are likely to hatch, at least in part, by comparing the measured optical density of respective insect eggs to a predetermined threshold for optical density.

* * * * *